(12) United States Patent
Terada et al.

(10) Patent No.: US 7,423,816 B2
(45) Date of Patent: Sep. 9, 2008

(54) SOLID IMMERSION LENS AND MICROSCOPE

(75) Inventors: Hirotoshi Terada, Hamamatsu (JP); Ikuo Arata, Hamamatsu (JP); Shigeru Sakamoto, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 790 days.

(21) Appl. No.: 10/804,194

(22) Filed: Mar. 19, 2004

(65) Prior Publication Data
US 2007/0183057 A1   Aug. 9, 2007

(30) Foreign Application Priority Data

| Mar. 20, 2003 | (JP) | ............................. 2003-078819 |
| May 23, 2003 | (JP) | ............................. 2003-146620 |
| Oct. 31, 2003 | (JP) | ............................. 2003-373059 |

(51) Int. Cl.
   *G02B 3/02*   (2006.01)
(52) U.S. Cl. ........................ 359/708; 359/661; 359/664
(58) Field of Classification Search ......... 359/656–661, 359/708, 718–719, 368, 808–811
See application file for complete search history.

(56) References Cited

U.S. PATENT DOCUMENTS

| 2,809,554 | A | * | 10/1957 | Bernhardt | ................... | 359/661 |
| 4,497,550 | A | * | 2/1985 | Ouchi et al. | ................ | 359/509 |
| 4,634,234 | A | * | 1/1987 | Baumann | ................... | 359/661 |
| 5,004,307 | A | | 4/1991 | Kino et al. | ................... | 350/1.2 |
| 5,125,750 | A | | 6/1992 | Corle et al. | ................ | 359/819 |
| 5,208,648 | A | | 5/1993 | Batchelder et al. | .......... | 356/237 |
| 5,220,403 | A | | 6/1993 | Batchelder et al. | .......... | 356/345 |
| 5,422,498 | A | | 6/1995 | Nikawa et al. | ................ | 257/48 |
| 5,939,709 | A | | 8/1999 | Ghislain et al. | ............. | 250/216 |
| 6,002,792 | A | | 12/1999 | Oguri et al. | ................ | 382/145 |
| 6,369,957 | B1 | | 4/2002 | Ishida | | |
| 6,441,359 | B1 | | 8/2002 | Cozier et al. | ................ | 250/216 |

(Continued)

FOREIGN PATENT DOCUMENTS

EP    0 977 192 A1    2/2000

(Continued)

OTHER PUBLICATIONS

ISTFA, Nov. 2003, "Conference Proceedings from the 29th International Symposium for Testing and Failure Analysis", pp. 325-329.

(Continued)

*Primary Examiner*—Ricky L Mack
*Assistant Examiner*—James R Greece
(74) *Attorney, Agent, or Firm*—Drinker Biddle & Reath LLP

(57) ABSTRACT

A solid immersion lens 1 comprises a spherical portion 2 and a bottom surface portion 3. The bottom surface portion 3 is attached in close contact with a substrate 10 of a semiconductor device to be an observed object. The bottom surface portion 3 of this solid immersion lens 1 is formed in a cylindrical shape. Thereby, a solid immersion lens which can be easily separated from the observed object after an observation and can, during an observation, allow a light flux with a high NA to pass and a microscope using the same can be obtained.

10 Claims, 19 Drawing Sheets

U.S. PATENT DOCUMENTS

| | | |
|---|---|---|
| 6,475,398 B2 | 11/2002 | Kitahata ................. 216/2 |
| 6,560,030 B2 | 5/2003 | Legrand et al. |
| 6,594,086 B1 * | 7/2003 | Pakdaman et al. ........ 359/656 |
| 6,608,359 B2 | 8/2003 | Kitahata ................. 257/432 |
| 6,621,275 B2 | 9/2003 | Cotton et al. ............ 324/537 |
| 6,656,029 B2 | 12/2003 | Kitahata ................. 451/384 |
| 6,687,058 B1 | 2/2004 | Ippolito et al. ........... 359/656 |
| 6,778,327 B2 * | 8/2004 | Pakdaman et al. ........ 359/656 |
| 6,831,782 B2 | 12/2004 | Patton et al. |
| 6,944,112 B2 | 9/2005 | Challener |
| 2001/0050896 A1 | 12/2001 | Hajjar et al. |
| 2003/0202255 A1 * | 10/2003 | Pakdaman et al. ........ 359/656 |
| 2003/0210057 A1 | 11/2003 | Cotton et al. ............ 324/501 |
| 2007/0146871 A1 | 6/2007 | Terada et al. |

FOREIGN PATENT DOCUMENTS

| | | |
|---|---|---|
| JP | 05-157701 | 6/1993 |
| JP | 06-300824 | 10/1994 |
| JP | 7-18806 | 3/1995 |
| JP | 07-190946 | 7/1995 |
| JP | 8-315404 | 11/1996 |
| JP | 11-003534 | 1/1999 |
| JP | 11-202194 | 7/1999 |
| JP | 11-203711 | 7/1999 |
| JP | 2000-11423 | 1/2000 |
| JP | 2000-121930 | 4/2000 |
| JP | 2000-235038 | 8/2000 |
| JP | 2001-023230 | 1/2001 |
| JP | 2002-512697 | 4/2002 |
| JP | 2002-189000 | 7/2002 |
| JP | 2002-236087 | 8/2002 |
| JP | 2003-130781 | 5/2003 |
| JP | 2003-141768 | 5/2003 |
| WO | WO 98/58288 | 12/1998 |

OTHER PUBLICATIONS

ISTFA 2003, "Photoemission and Obirch Analysis with Solid Immersion Lens (SIL)", pp. 1-20.

* cited by examiner

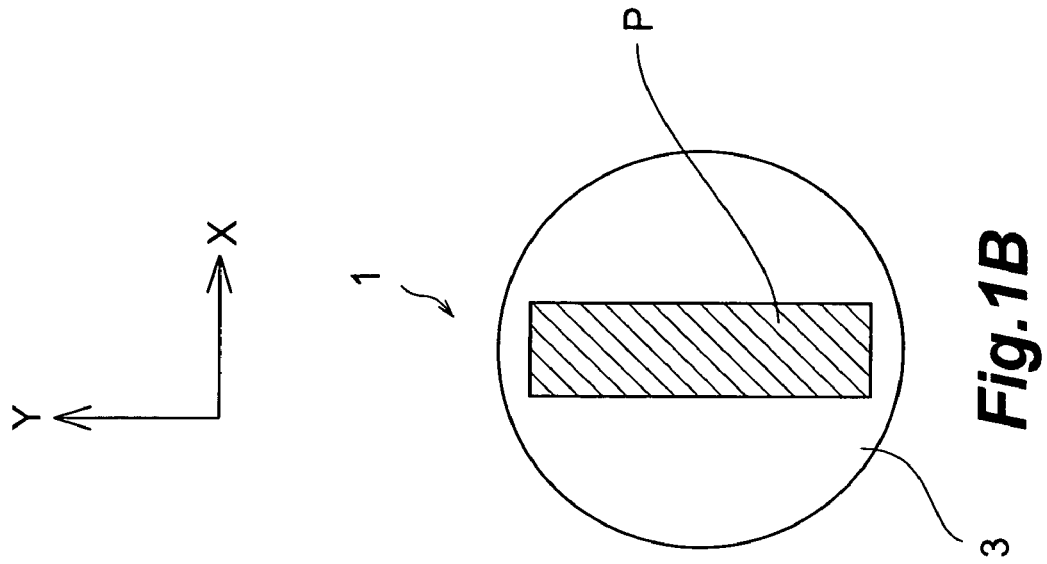
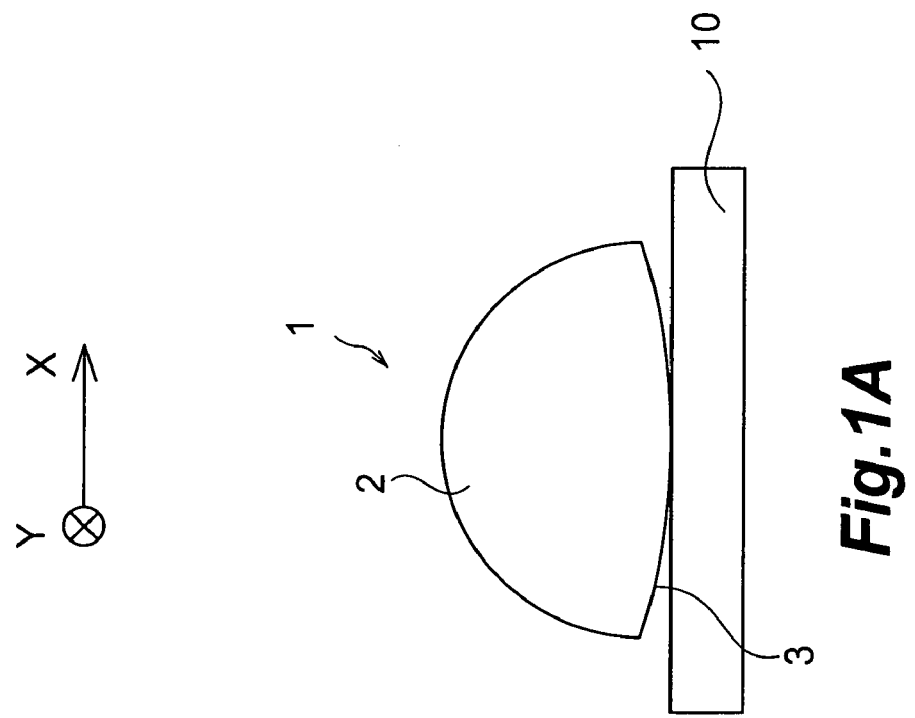

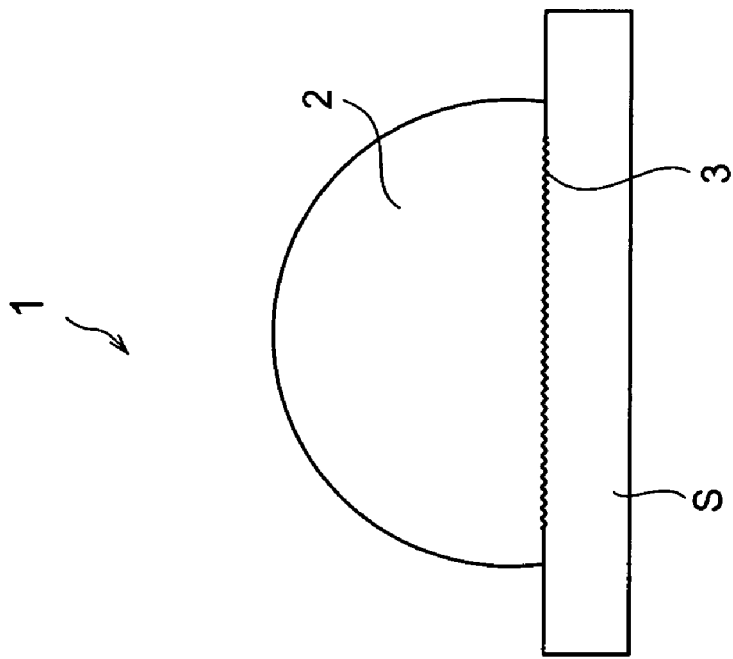
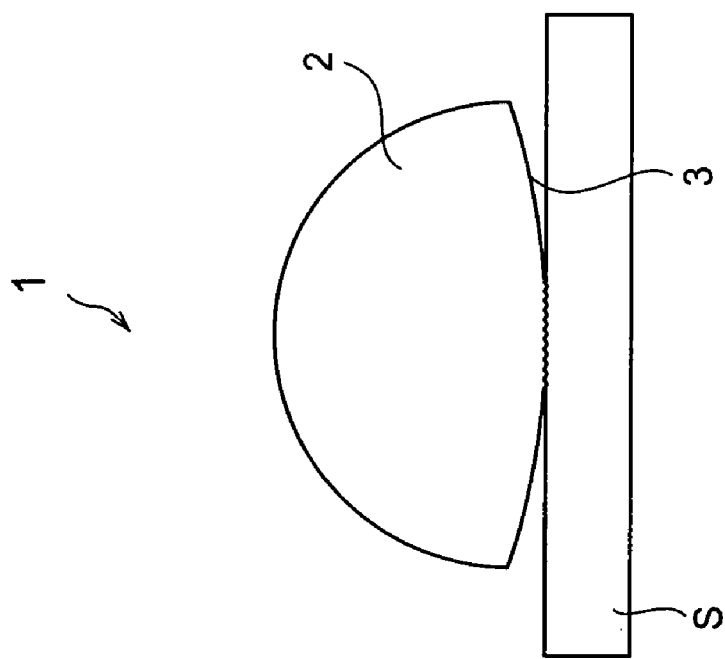

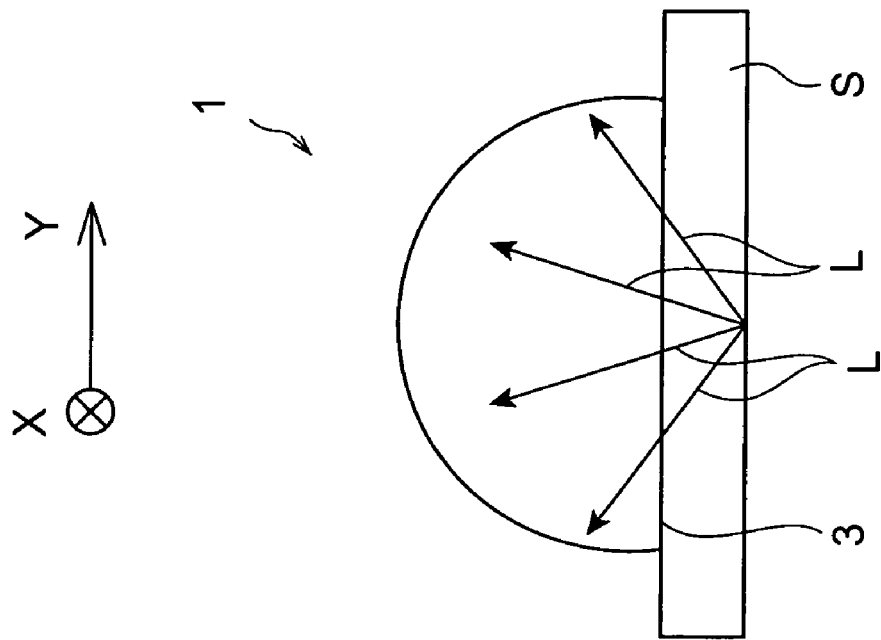
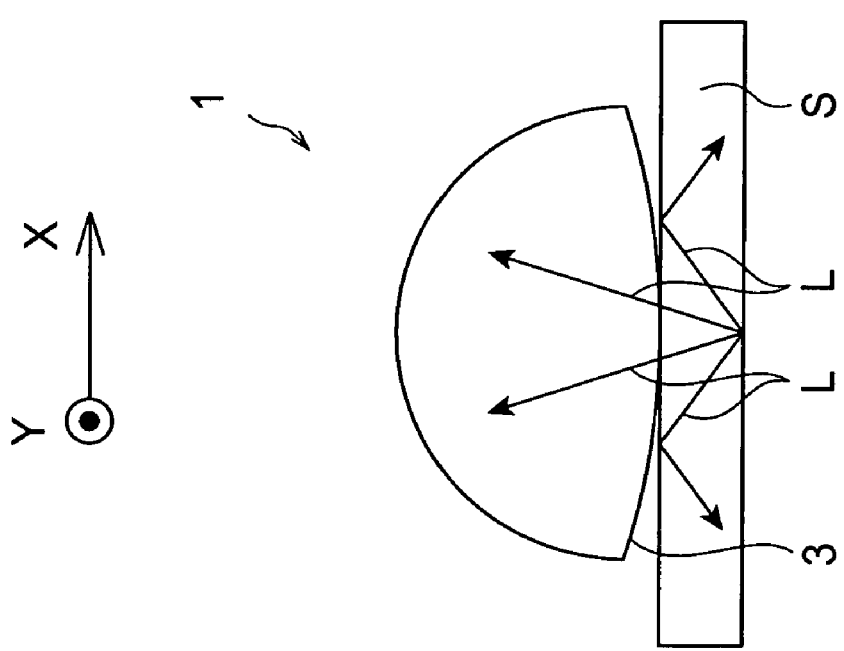
Fig.5A
Fig.5B

SOLID IMMERSION LENS AND MICROSCOPE

BACKGROUND OF THE INVENTION

1. Field of the Invention

The present invention relates to a solid immersion lens and a microscope to be used for a method for inspecting electronic devices, for example, which is employed for failure analysis of electronic devices and for reliability evaluation thereof.

2. Related Background of the Invention

In an inspection of electronic devices, a method for observing an electronic device as a sample by a microscope has been employed. Conventionally, an emission microscope and an IR-OBIRCH apparatus, etc., have been known as electronic device inspection apparatuses (cf. Japanese Patent Application Laid-Open No. H7-190946 and Japanese Patent Application Laid-Open No. H6-300824). However, in recent years, miniaturization of electronic devices, which are inspected objects, has been advanced, and in prior-art inspection apparatuses employing visible light, infrared light, or heat rays, it has become difficult to analyze the microstructure due to restrictions resulting from a diffraction limit in an optical system.

Therefore, in a case where an abnormal point generated in circuit patterns such as transistors and wiring, which are formed in an electronic device, is detected by analyzing such a microstructure of an electronic device, such a method has been used, in which the range where the abnormal point exists is first narrowed to some extent by an inspection apparatus employing visible light, infrared light, or heat rays, then the narrowed range is observed by use of an observation apparatus such as an electron microscope having a higher resolution, and thereby the abnormal point in the electronic device is inspected.

As described above, in the method where a high-resolution observation is carried out by an electron microscope after an inspection using light is carried out, there is a problem in that the inspection of electronic devices requires a great deal of work and time due to such a reason, that is, preparation and installation of electronic devices of the targets of the inspection being complicated and cumbersome.

On the other hand, a solid immersion lens (SIL) has been known as a lens for enlarging an image of an observed object. The solid immersion lens is generally known as a hemispherical lens or a lens with a hyperhemispherical form called a Weierstrass sphere. By installing this solid immersion lens on the surface of an observed object, both the numerical aperture NA and magnification can be enlarged, thus an observation with a high resolution becomes possible. As semiconductor inspection apparatuses using such solid immersion lenses, for example, those described in Japanese Patent Publication No. H7-18806 and the specification of U.S. Pat. No. 6,594,086 exist. In addition, description of a solid immersion lens also exists in Japanese Patent Application Laid-Open No. 2002-189000.

SUMMARY OF THE INVENTION

The solid immersion lens disclosed in Japanese Patent Publication No. H7-18806 is a plano-convex lens, whose attaching surface (bottom surface) to an observed object is a plane. In an observation using a solid immersion lens, if a gap occurs between the solid immersion lens and a semiconductor substrate, an incident light with a critical angle or more is totally reflected, only an incident light with a critical angle or less is propagated, and an effective numerical aperture is limited by the critical angle. However, if the gap between the solid immersion lens and rear surface of the semiconductor substrate becomes equivalent to a light wavelength of the inside of the semiconductor, light can be propagated by evanescent coupling.

However, in the gap between the plano-convex lens and rear surface of the semiconductor substrate, a part with a great gap exists as a result of a wide confronting region, and in such a part with a great gap, transmitted light sharply declines in intensity, only an incident light with a critical angle or less can be propagated, and an effective numerical aperture is limited. As such, in an inspection using a plano-convex lens, since surface accuracy of the bottom surface of the plano-convex lens is required to be of a high accuracy, this causes an increase in the manufacturing cost. Furthermore, since surface accuracy of a contact surface is required for the semiconductor substrate as well, a problem exists such that a pretreatment (polishing of the semiconductor substrate) for inspecting the semiconductor device requires a great deal of labor.

In addition, even if the surface accuracy of the contact surfaces can be made of high accuracy in the plano-convex lens and substrate, when these are optically coupled, since air flow resistance is high, a problem also exists such that it takes a long time to attain optical coupling.

Therefore, in Japanese Patent Publication No. H7-18806, as a method for obtaining an intrinsic resolution of a solid immersion lens, a method utilizing index matching by interposing a high refractive index fluid between the plano-convex lens and observed object has been described. This is a method utilizing index matching and is different from a method utilizing evanescent coupling. As a representative high-refractive-index matching fluid, an arsenic tribromide/disulfide/selenium compound base can be mentioned, however, since arsenic tribromide has toxicity and causticity, a problem exists in handling.

In addition, the solid immersion lens disclosed in the specification of U.S. Pat. No. 6,594,086 is a bi-convex lens. In this lens, since the attaching surface has a convex shape to make contact with an observed object at a point (point of contact), this is considered to be advantageous in securing optical connectivity compared to the plano-convex lens. However, since the contact area with an observed object is very small, if the substrate of a semiconductor device to be an observed object thickens, this cannot allow a light flux with a high NA to pass any longer, therefore, a problem has existed such that a high resolution and a high light-condensing ability intrinsic to the solid immersion lens cannot be obtained.

In order to closely fit this solid immersion lens and the observed object with a wide area, it is necessary to apply pressure between the bottom surface of the solid immersion lens and observed object. Herein, as shown in FIG. 8, the smaller the radius of curvature of the lens becomes, the higher the pressure required for close fitting becomes. FIG. 8 shows a pressure required for closely fitting the bottom surface of the solid immersion lens, up to a diameter of 2 mm, to a plane portion of the observed object. In a rear surface analysis of a semiconductor device using the solid immersion lens, the semiconductor substrate must be pressurized while the strength in handling is sufficiently considered. This is because integrated circuits formed on the front surface of the semiconductor substrate may be damaged if an excessive pressure is applied. When the tendency of thinning of semiconductor devices is taken into account, the intrinsic resolution of a solid immersion lens cannot be obtained with a bi-convex lens.

In addition, although distortion occurs in the semiconductor device due to the pressure, since this condition is different from a semiconductor device mounted condition, a demand for carrying out an inspection on operating conditions similar to those of the mounted condition cannot be satisfied. In the condition with distortion, even a possibility to cause a result contrary to the original object of the inspection exists.

Furthermore, in this lens, owing to the characteristics in terms of its shape, a problem exists such that a positional relationship with the semiconductor substrate is not uniquely determined. If the lens is attached with inclination to the contact surface of the semiconductor substrate, optical coupling at a center portion of the solid immersion lens bottom surface cannot be obtained. For avoidance thereof, an accurate positional control of the solid immersion lens is required, thus causing an increase in size of the apparatus and high costs.

Therefore, it is an object of the present invention to provide a solid immersion lens which can allow a light flux with a high numerical aperture to pass and, furthermore, whose positional control is simple when optically coupling the same with an observed object and a microscope using the same.

A solid immersion lens according to the present invention whereby the above-described object is achieved is a solid immersion lens attached to an observed object and to be used for an observation of the observed object, wherein an attaching surface to the observed object is formed in a toroidal shape.

In the solid immersion lens according to the present invention, the attaching surface to an observed object is formed in a toroidal shape. Concretely, the bottom surface of the solid immersion lens is an aspherical surface (toroidal surface) which is not an optical-axis-symmetric surface of revolution, and one axis (base axis) thereof forms a shape to optically couple with an observed object. The base axis to form a shape appropriate for optical coupling is a straight line or an arc with a great radius of curvature. On the other hand, the other axis is an arc with a small radius of curvature in comparison with the base axis to form a shape suitable for optical coupling, and forms a shape favorable for attachment and detachment of the solid immersion lens. Here, in the present invention, a curved surface whose base axis to form a shape appropriate for optical coupling is a straight line and whose other axis is an arc, namely, a cylindrical shape (cylindrical surface) is also included in the toroidal shape (toroidal surface).

Accordingly, since an optically coupled region appears in a band form along the base line to form a straight line or an arc with a great radius of curvature, this can allow a light flux with a high NA to pass. In addition, since the solid immersion lens is, along the base axis of its bottom surface, brought into contact with the observed object, positional control of the solid immersion lens is simplified. Furthermore, since the optical coupling can be released, after an observation, by an extremely weak force from a lateral side of the base line to the solid immersion lens, there is no danger of damaging the observed object and solid immersion lens when the solid immersion lens is detached.

Herein, it is preferable to employ a mode wherein, when a to-be-attached surface of the observed object is set to an X-Y plane, a ratio of a radius of curvature in the X-direction of the toroidal shape to a radius of curvature in the Y-direction greater than the radius of curvature in the X-direction is provided as $1:3 \sim 1:\infty$.

By providing a toroidal shape to have a radius of curvature of this range, since an optically coupled region appears in a band form along the Y-direction to form an arc with a great radius of curvature, this can allow a light flux with a high NA to pass. In addition, since the solid immersion lens is brought into contact with the observed object along the Y-direction of its bottom surface, positional control of the solid immersion lens is simplified. Furthermore, since the optical coupling can be released, after an observation, by an extremely weak force from a lateral side of the Y-direction to the solid immersion lens, there is no danger of damaging the observed object and solid immersion lens when the solid immersion lens is detached.

Here, the reason that the ratio of a radius of curvature in the X-direction of the toroidal shape to a radius of curvature in the Y-direction greater than the radius of curvature in the X-direction is provided as $1:3 \sim 1:\infty$ is that the optical coupling ability when the lens is closely fitted to the observed object may become insufficient if the radius of curvature in the Y-direction is less than three times the radius of curvature in the X-direction. In addition, when the radius of curvature in the X-direction of the toroidal shape to the radius of curvature in the Y-direction becomes $1:\infty$, the toroidal shape becomes a cylindrical shape.

In addition, a microscope according to the present invention is a microscope for observing an observed object (sample), comprising: an optical system for leading an image of the observed object, including an objective lens into which light from the observed object is made incident; and the above-mentioned solid immersion lens. Thereby, a microscope which is capable of suitably observing a sample can be obtained. Here, as the observed object, an electronic device in a case where an electronic device inspection is carried out can be mentioned, for example. In addition, an image acquisition means for acquiring an image of a sample of an observed object led by the optical system may be provided for the optical system and solid immersion lens.

BRIEF DESCRIPTION OF THE DRAWINGS

FIG. 1A and FIG. 1B are a (A) side view and a (B) rear view showing a condition where a solid immersion lens according to the present embodiment has been attached to a semiconductor substrate.

FIG. 3A and FIG. 3B are a (A) side view and a (B) front view showing a close fitting condition between a solid immersion lens and a semiconductor device.

FIG. 5A and FIG. 5B are a (A) side view and a (B) front view showing a condition where light is transmitted from a semiconductor device to a solid immersion lens.

DESCRIPTION OF THE PREFERRED EMBODIMENTS

Figure 2:
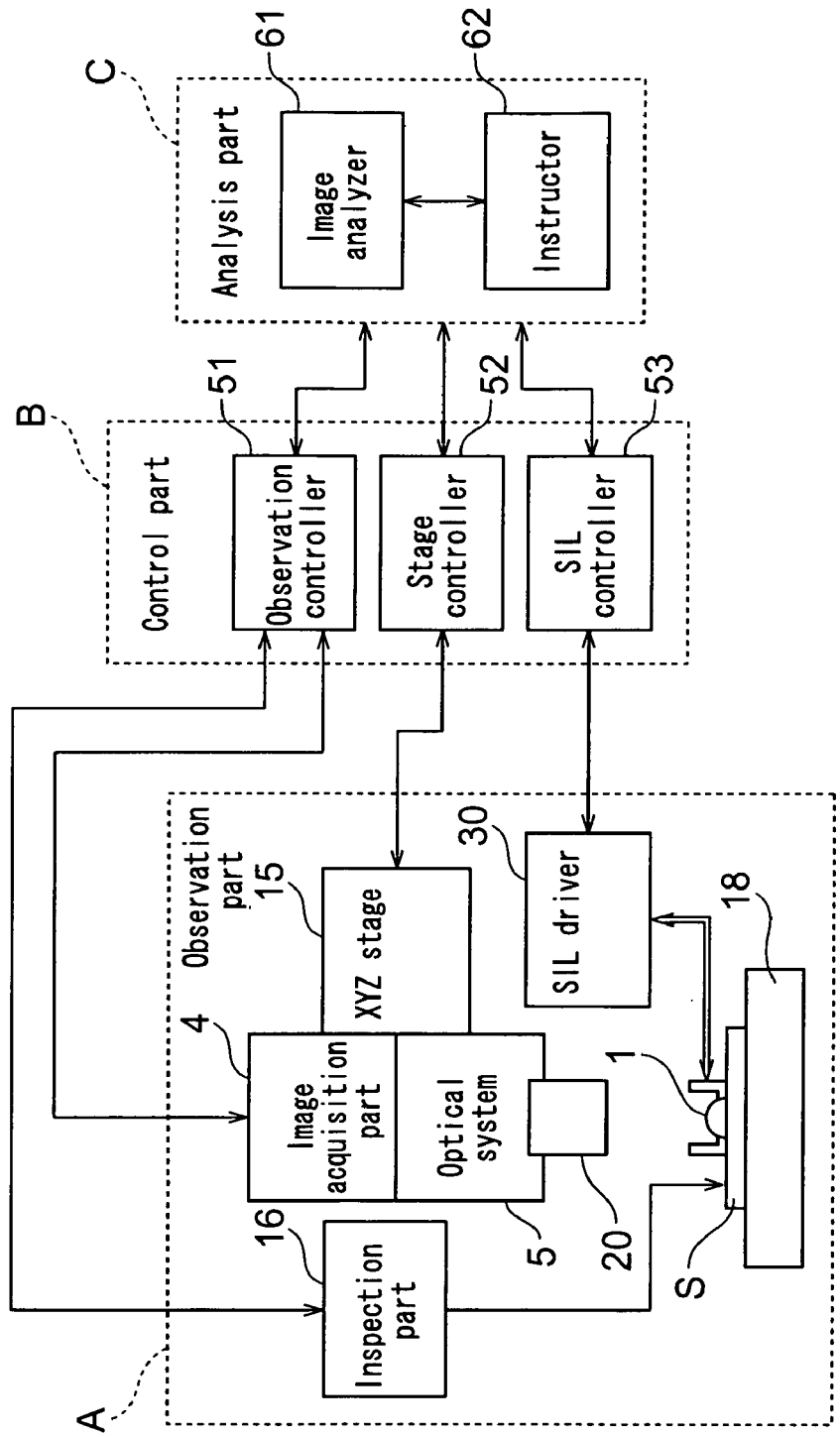
FIG. 2 is a block diagram showing a semiconductor inspection apparatus having a solid immersion lens according to the present embodiment.

Hereinafter, preferred embodiments of the present invention will be described with reference to the drawings. Here, in the respective embodiments, identical symbols will be used for parts having identical functions, whereby overlapping description will be omitted. In addition, the dimensional ratios of the drawings are not always coincident with those of the description.

FIG. 1A and FIG. 1B are views showing a condition where a solid immersion lens according to the present embodiment has been attached to a semiconductor substrate, wherein FIG. 1A is a side view and FIG. 1B is a rear view.

A solid immersion lens 1 according to the present embodiment is used while being attached to a substrate of a semiconductor device to be an observed object (inspected object). In a rear surface analysis of a semiconductor device using a solid immersion lens, by optically coupling the solid immersion lens to a semiconductor substrate, the semiconductor substrate itself is used as a part of the solid immersion lens. According to this method, when an objective lens is focused on an integrated circuit formed on the surface of the semiconductor substrate, since an effect of the solid immersion lens can prevent the focal position from becoming deeper than that in the air, a decline in the effective numerical aperture can be suppressed, and a higher resolution by a shorter wavelength can be expected.

As shown in FIG. 1A and FIG. 1B, the solid immersion lens 1 according to the present embodiment comprises a spherical portion 2 and a bottom surface portion 3 to be an attaching surface of the present invention.

In addition, the bottom surface portion 3 has a cylindrical shape. This bottom surface portion 3 of the solid immersion lens 1 is attached by close fitting to the rear-side surface of a substrate (hereinafter, referred to as a "semiconductor substrate") 10 of a semiconductor device, which is an observed object. The surface of the semiconductor substrate 10 to be a to-be-attached surface of the present invention has a plane shape, and as shown in FIG. 1B, when X-Y coordinates are set on a face corresponding to the surface of the semiconductor substrate 10, the radius of curvature in the X-direction of the bottom surface portion 3 of the solid immersion lens 1 to the radius of curvature in the Y-direction is provided as 1:∞. In addition, an optically coupled region P between the bottom surface portion 3 of the solid immersion lens 1 and semiconductor substrate 10 appears in a band form along the base axis of the cylindrical surface.

Furthermore, the shape of the spherical portion 2 of the solid immersion lens 1 is determined by conditions to eliminate aberrations. Now, where the radius of the solid immersion lens 1 is provided as R and the refractive index is provided as n, the solid immersion lens 1 having a hemispherical form has an object point having no aberration at its sphere center, and at this time, the numerical aperture NA and magnification both become n times. On the other hand, in a solid immersion lens having a hyperhemispherical form, a position shifted downward by R/n from the sphere center becomes an object point having no aberration, and at this time, the numerical aperture NA and magnification both become $n^2$ times. Or, the solid immersion lens 1 may be installed according to specific observation conditions, etc., for a semiconductor device S, such that a position between the sphere center and the position shifted downward by R/n from the sphere center is determined as a focal point.

In addition, when an inspection of a semiconductor device is carried out, as a material of the solid immersion lens of the present invention, a high refractive index material substantially identical to a substrate material of the semiconductor device or close to its refractive index is preferably used. As examples thereof, Si, GaP, GaAs, etc., can be mentioned. Here, if the substrate is made of glass or plastic, as the solid immersion lens material, glass or plastic is preferably selected.

Next, together with a method for inspecting a semiconductor device using a solid immersion lens according to the present embodiment, actions of a solid immersion lens according to the present embodiment will be described. A semiconductor inspection apparatus employed in this inspecting method is an inspection apparatus whose inspected object is, for example, a semiconductor device provided by forming circuit patterns made up of transistors and wiring, etc., on a semiconductor substrate and which obtains an image of the semiconductor device to inspect internal data thereof.

First, an inspection apparatus to be employed in the semiconductor device inspecting method will be described. FIG. 2 is a block diagram of a semiconductor inspection apparatus having a solid immersion lens according to the present embodiment. Herein, although a microscope using a solid immersion lens according to the present invention is generally applicable to a case where a sample of an observed object is observed, in the following, description will be given mainly of a semiconductor inspection apparatus (electronic device inspection apparatus) and inspecting method, which is an application example thereof.

As shown in FIG. 2, a semiconductor inspection apparatus according to the present embodiment comprises an observation part A for observing a semiconductor device S, a control part B for controlling operations of respective portions of the observation part A, and an analysis part C for processing and instructions necessary for an inspection of the semiconductor device S. In addition, a semiconductor device S to be an inspected object of the semiconductor inspection apparatus according to the present embodiment is placed on a stage 18 provided in the observation part A.

The observation part A has an image acquisition part 4 installed in a black box (unillustrated), an optical system 5, and a solid immersion lens 1 according to the present embodiment. The image acquisition part 4 is made up of, for example, a photodetector and an imaging apparatus, etc., and is a means for picking up an image of the semiconductor device S. In addition, between the image acquisition part 4 and semiconductor device S placed on the stage 18, the optical system 5 to lead an image of light from the semiconductor device S to the image acquisition part 4 is provided.

In the optical system 5, at a predetermined position thereof opposed to the semiconductor device S, an objective lens 20 into which light from the semiconductor device S is made incident is provided. Light emitted or reflected from the semiconductor device S is made incident into the objective lens 20 and reaches the image acquisition part 4 via the optical system 5 including this objective lens 20. Then, in the image acquisition part 4, an image of the semiconductor device S used for an inspection is picked up.

The image acquisition part 4 and optical system 5 are integrally constructed in a condition where their optical axes are made coincident to each other. In addition, for the image acquisition part 4 and optical system 5, an XYZ stage 15 is installed. Thereby, the image acquisition part 4 and optical system 5 are constructed so as to be capable of positioning and focusing with respect to the semiconductor device S by being shifted according to need in the X and Y directions (horizontal direction) and Z-direction (vertical direction), respectively.

In addition, for the semiconductor device S to be an inspected object, an inspection part 16 is provided. The inspection part 16 carries out state control, etc., of the semiconductor device S according to need when carrying out an inspection of the semiconductor device S. A method for controlling the state of the semiconductor device S by the inspection part 16 is different depending on a concrete inspecting method to be applied to the semiconductor device S, and for example, a method of supplying a voltage to a predetermined part of circuit patterns formed on the semiconductor device S or a method of irradiating laser light to be a probe light to the semiconductor device S or the like can be employed.

In addition, in the observation part A, a solid immersion lens (SIL) 1 is further installed. In the semiconductor inspection apparatus, this solid immersion lens 1 is installed so as to be movable with respect to the image acquisition part 4 and optical system 5 and the semiconductor device S placed on the stage 18. Concretely, the solid immersion lens 1 is constructed so as to be movable between an insertion position where the same includes an optical axis from the semiconductor device S to the objective lens 20, and is installed while being closely fitted to the surface of the semiconductor device S as described above, and a position (standby position) off the optical axis.

Furthermore, for the solid immersion lens 1, a solid immersion lens (SIL) driver 30 is provided. The solid immersion lens driver 30 is a drive means for driving and shifting the solid immersion lens 1 between the above-described insertion position and standby position. In addition, the solid immersion lens driver 30 adjusts the insertion position of the solid immersion lens 1 with respect to the objective lens 20 of the optical system 5 by minutely shifting the position of the solid immersion lens 1. Here, in FIG. 2, the solid immersion lens 1 is shown in a condition where the same has been installed at the insertion position between the objective lens 20 and semiconductor device S.

For the observation part A for carrying out an observation, etc., to inspect the semiconductor device S, the control part B and analysis part C are provided.

The control part B has an observation controller 51, a stage controller 52, and a solid immersion lens (SIL) controller 53. The observation controller 51 controls execution of an observation of the semiconductor device S carried out in the observation part A and setting of observational conditions by controlling operations of the image acquisition part 4 and inspection part 16.

The stage controller 52 controls setting of an observation point of the semiconductor device S by the image acquisition part 4 and optical system 5, which is to be an inspection point of the present inspection apparatus or positioning, focusing and the like thereof by controlling operations of the XYZ stage 15. In addition, the solid immersion lens controller 53 controls, by controlling operations of the solid immersion lens driver 30, movement of the solid immersion lens 1 between the insertion position and standby position or an adjustment of the insertion position of the solid immersion lens 1.

The analysis part C has an image analyzer 61 and an instructor 62. The image analyzer 61 carries out necessary analyzing processes, etc., for an image picked up by the image acquisition part 4. In addition, the instructor 62 refers to input contents from an operator and analysis contents by the image analyzer 61 and carries out, via the control part B, necessary instructions related to execution of an inspection of the semiconductor device S in the observation part A.

In particular, in the present embodiment, in response to that the solid immersion lens 1 and solid immersion lens driver 30 are installed in the observation part A, the analysis part C carries out necessary processes and instructions related to an inspection of the semiconductor device S by use of a solid immersion lens.

Namely, in a case where the solid immersion lens 1 is inserted between the objective lens 20 and semiconductor device S, in the observation part A, the image acquisition part 4 acquires an image including reflected light from the solid immersion lens 1 in a condition where the solid immersion lens 1 exists at the insertion position. In addition, in the analysis part C, the image analyzer 61 carries out, for the image including reflected light from the solid immersion lens 1 obtained by the image acquisition part 4, a predetermined analysis such as determining a center of gravity position of its reflected light image. Then, the instructor 62 refers to the image including reflected light from the solid immersion lens 1 analyzed by the image analyzer 61 and instructs the solid immersion lens controller 53 to adjust the insertion position of the solid immersion lens 1 so that the center of gravity position of the reflected light image coincides with the inspection point in the semiconductor device S.

Now, description will be given of a method for inspecting a semiconductor device (sample observation method) according to the present embodiment.

First, for the semiconductor device S of an inspected object, an observation is carried out in a condition where the solid immersion lens 1 has been installed at the standby position off the optical axis. Herein, by the image acquisition part 4, a pattern image of the circuit patterns which is an observation image of the semiconductor device S is acquired via the optical system 5 including the objective lens 20. In addition, the semiconductor device S state is controlled to be a predetermined condition by the inspection part 16, and an abnormality observation image for detecting an abnormal point of the semiconductor device S is acquired.

Next, by use of the pattern image and abnormality observation image picked up by the image acquisition part 4, whether an abnormal point exists in the semiconductor device S is examined. If an abnormal point exists, the position thereof is detected, and the detected abnormal point is set as an inspection point (an observation point by an microscope) by a semiconductor inspection apparatus. And, the image acquisition part 4 and optical system 5 are moved by the XYZ stage 15 so that the set inspection point is positioned at the center of an image obtained by the image acquisition part 4.

Subsequently, the solid immersion lens 1 is to be installed at the inspection point judged to be an abnormal point in the semiconductor device S, and the solid immersion lens 1 is to be inserted between the semiconductor device S and objective lens 20, wherein before installing the solid immersion lens 1, an optical contact liquid is dripped on the inspection point to wet the inspection point of the semiconductor device S. This optical contact liquid is made of water containing amphipathic molecules. Since the optical contact liquid contains amphipathic molecules, this lowers the surface tension on the semiconductor substrate, which is a hydrophobic surface. As a result, the hydrophobic surface is improved in wettability, and the optical contact liquid spreads on the semiconductor device S.

As the amphipathic molecules herein used, surfactant molecules are preferably used. In addition, as the surfactant molecules, ionic surfactant molecules and nonionic surfactant molecules can be used. As an ionic surfactant, any of a cationic surfactant, an anionic surfactant, and an ampholytic surfactant can be used.

Surfactants are generally used for a variety of uses as wetting agents, penetrating agents, foaming agents, antifoaming agents, emulsifying agents, antistatic agents and the like, and in the present invention, in addition to those having a wetting property related to wettability, those having an antifoaming property to suppress foaming and an antistatic property to suppress electrification are preferable. Use of a surfactant having an antistatic ability can prevent air embracing due to electrification. In addition, use of a surfactant having an antifoaming property can prevent foaming due to mechanical conveyance or stirring when the optical contact liquid is supplied.

In addition, the optimum concentration range of a surfactant is preferably provided to be greater than 0 times and not more than 400 times with respect to a critical micelle concentration of the surfactant. This is because if the concentration is greater than 400 times, viscosity of the optical contact liquid tends to increase excessively and by contrast, optical coupling may be hindered. In addition, a more preferable range thereof is 0.5-100 times with respect to a critical micelle concentration of the surfactant. This is because if the concentration is smaller than 0.5 times, surface tension of the optical contact liquid may not be lowered sufficiently, and if the concentration exceeds 100 times, viscosity of the optical contact liquid tends to increase excessively. For the same reason, a further preferable range thereof is a concentration range of 1 time-10 times with respect to a critical micelle concentration of the surfactant.

Here, the optical contact liquid used in the present embodiment is not limited to one containing surfactant molecules, and the molecules may be those having both hydrophilic groups (such as carboxyl group, sulfo groups, quaternary ammonium groups, hydroxyl groups) and hydrophobic groups (also called lipophilic groups. Such as long-chain hydrocarbon groups). For example, wetting agents of glycerin, propylene glycol, sorbitol and the like, phospholipids, glycolipids, aminolipids and the like can be mentioned.

In a condition where a semiconductor substrate and a solid immersion lens have been optically coupled by use of the above-described optical contact liquid, it is considered that van der Waals force works between the hydrophilic groups of amphipathic molecules physically adsorbed on the semiconductor substrate and water molecules and the water molecules are restrained to stop volatilization. At this time, the distance between the solid immersion lens and semiconductor substrate can be provided as $1/20\lambda$ ($\lambda$: irradiation wavelength) or less, for example, and as a result, optical contact between the solid immersion lens and semiconductor substrate, and furthermore, physical anchoring are achieved. Here, the "optical contact" mentioned in the present invention means a condition where optical coupling is achieved between the semiconductor substrate and solid immersion lens by evanescent coupling.

In addition, as an optical coupling material other than the above-described optical contact liquid, for example, as described in Japanese Patent Publication No. H7-18806, a refractive index matching fluid (such as an index matching fluid) for refractive index matching of a solid immersion lens and a semiconductor substrate can be mentioned. Here, the refractive index matching fluid and the optical contact liquid are different, and the former realizes a high NA via the fluid refractive index, while the latter has a role to assist evanescent coupling. Herein, although an embodiment using the optical contact liquid is described in detail, similar effects can be obtained even in an embodiment using the refractive index matching fluid. However, in such a case, since it is not always necessary to dry the fluid, a drying gas supplying means can be omitted depending on the embodiment.

Once the optical contact liquid has spread on the semiconductor substrate, before the optical contact liquid dries, the solid immersion lens 1 is installed, and after the solid immersion lens 1 is inserted between the semiconductor device S and objective lens 20, the insertion position of the solid immersion lens 1 is adjusted.

Herein, since the optical contact liquid contains amphipathic molecules, this can provide wettability for the substrate surface of the semiconductor device S and attaching surface of the solid immersion lens 1. In addition, when installing the solid immersion lens 1, empty weight of the solid immersion lens 1 is utilized. Accordingly, it is possible to easily install the minute solid immersion lens 1 at a desirable position of the semiconductor substrate surface without applying an excessive pressure. First, by the image acquisition part 4, an image including reflected light from the solid immersion lens 1 is picked up. Adjustment of the insertion position of the solid immersion lens 1 is carried out while using, as a guide, reflected lights from respective reflecting surfaces of the solid immersion lens 1 in a reflected light image included in this image.

When carrying out the adjustment of the insertion position of the solid immersion lens 1, in the image analyzer 61, automatically or upon an instruction from the operator, an analysis is carried out for an image including reflected light from the solid immersion lens 1, whereby a center of gravity position of the reflected light image is determined. In addition, in the instructor 62, via the solid immersion lens controller 53, to the solid immersion lens 1 and solid immersion lens driver 30, an adjustment of the insertion position of the solid immersion lens 1 is instructed so that the center of gravity position of the reflected light image obtained in the image analyzer 61 coincides with the inspection point in the semiconductor device S. Thereby, positioning of the solid immersion lens 1 with respect to the semiconductor device S and objective lens 20 is carried out.

Furthermore, the instructor 62 instructs, in line with the adjustment of the insertion position of the solid immersion lens 1 as described above, an adjustment of the distance between the semiconductor device S where the solid immersion lens 1 has been installed in a closely fitted manner and objective lens 20 of the optical system 5, via the stage controller 52, to the XYZ stage 15. Thereby, focusing in a condition where the solid immersion lens 1 has been inserted is carried out.

Thereafter, air is blown on the solid immersion lens 1 to vaporize and dry the optical contact liquid so as to optically closely fit the solid immersion lens 1 to the semiconductor substrate. Since the bottom surface portion 3 of the solid immersion lens 1 has been formed in a cylindrical shape, the solid immersion lens 1 makes line contact with the semiconductor device S. Concretely, as shown in FIG. 3A, the solid immersion lens 1 makes contact at only a point in the X-direction, and as shown in FIG. 3B, makes contact along the Y-direction as a whole. Here, in FIG. 3A and FIG. 3B, a contact position between the solid immersion lens 1 and semiconductor device S is shown by a wavy line.

In addition, for example, if the bottom surface portion of a solid immersion lens is formed so as to make contact with a semiconductor substrate at one point, in order to make the bottom surface portion of the solid immersion lens and semiconductor substrate contact with a wide area, it becomes necessary to apply a high pressure thereto. However, in the solid immersion lens 1 according to the present embodiment, the bottom surface portion 3 has been formed in a cylindrical shape. In addition, the optical contact liquid to assist evanescent coupling is used. Therefore, without applying a high pressure to the solid immersion lens 1, the bottom surface portion 3 and semiconductor device S can be optically coupled in a band form by only the empty weight of the solid immersion lens 1, for example, and furthermore, physical anchoring can be realized. Accordingly, since optical close fitting can be attained even without applying an excessive pressure to the semiconductor device, there is no danger of damaging the semiconductor device S.

Furthermore, in the solid immersion lens 1 according to the present embodiment, since the bottom surface portion 3 has been formed in a cylindrical shape, the center one-axis (base axis) direction always makes line-contact with the semiconductor device S. In contrast thereto, in a case of the bi-convex lens formed so that the bottom surface portion makes contact with the semiconductor substrate at one point, for example, when the solid immersion lens is provided on the semiconductor substrate with inclination, the center portion is not optically coupled. Accordingly, in the solid immersion lens 1 according to the present embodiment, optical coupling ability can be made satisfactory at its central portion. In addition, since the contact area of the solid immersion lens with the semiconductor substrate is greater than that of one-point contact, even when the substrate of the semiconductor device S is thick, a high-NA light flux can be secured. Furthermore, positioning is simplified.

Moreover, in the solid immersion lens 1 according to the present embodiment, since the bottom surface portion 3 has been formed in a cylindrical shape, vaporization of the optical contact liquid can be finished in a short time. When this point is explained with reference to FIG. 4A and FIG. 4B, if a solid immersion lens (plano-convex lens) 6 whose bottom surface portion 3 has a plane shape is used as shown in FIG. 4B, an optical contact liquid W is sandwiched between the solid immersion lens 6 and semiconductor device S and has open faces contributing to vaporization in only the lateral directions, therefore it takes time to vaporize the optical contact liquid W.

Figure 4A:
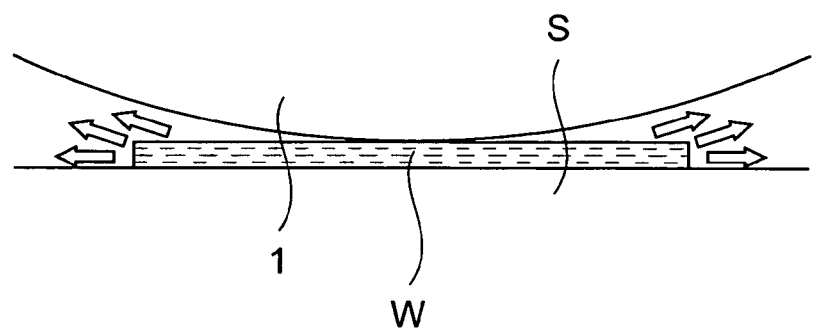
FIG. 4A is an enlarged sectional view showing the area between a solid immersion lens according to the present embodiment and a semiconductor device.
Figure 4B:
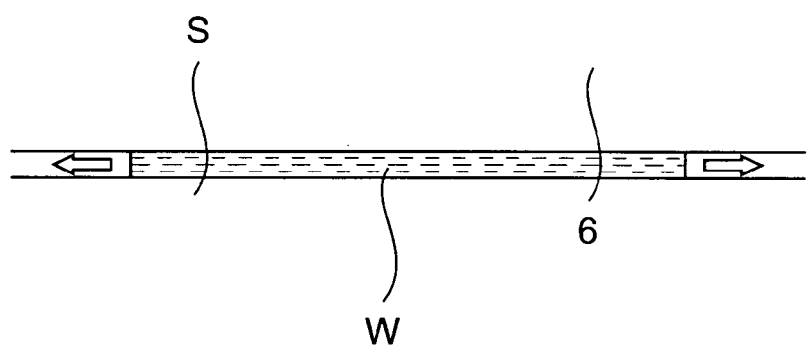
FIG. 4B is an enlarged sectional view showing the area between a solid immersion lens according to the prior art and a semiconductor device.

In contrast thereto, as shown in FIG. 4A, in the solid immersion lens 1 according to the present embodiment, owing to the bottom surface portion 3 formed in a cylindrical shape, the optical contact liquid W is vaporized toward a wide range. Therefore, vaporization can be finished in a short time, and the solid immersion lens 1 and semiconductor device S can be swiftly closely fitted and fixed.

Furthermore, by blowing air laterally with respect to the axial direction of the cylindrical shape of the bottom surface portion 3 of the solid immersion lens 1, the optical contact liquid can be more swiftly vaporized.

Thus, once the solid immersion lens 1 has been closely fitted to the semiconductor device S, an enlarged observation image of the semiconductor substrate is picked up via the optical system including the solid immersion lens 1. The observation image is obtained by leading of light from the semiconductor device led to the image acquisition part 4.

In addition, when obtaining an observation image, light from the semiconductor device S is transmitted through the optically closely fitted part between the semiconductor device S and solid immersion lens 1. Herein, since the solid immersion lens 1 has been securely closely fitted to the semiconductor device S in at least the Y-direction, close fitting of the central portion can be securely obtained. Accordingly, as shown in FIG. 5A, light L oriented in the X-direction is small in the amount of transmission through the solid immersion lens 1 since, in terms of a region where the gap between the solid immersion lens attaching surface and semiconductor substrate becomes greater than a light wavelength of the inside of the semiconductor, an incident light with a critical angle or more is totally reflected. In contrast thereto, as shown in FIG. 5B, light oriented in the Y-direction is securely transmitted through the solid immersion lens 1. As such, it is also possible to stabilize the direction of light being transmitted through the solid immersion lens 1.

Once an observation image has been obtained as such, after picking up an enlarged observation image, an optical contact liquid solvent (hereinafter, referred to as a "solvent") is dripped on the periphery of a position of the semiconductor device S where the solid immersion lens 1 has been attached to wet the attaching position of the solid immersion lens 1. By dripping the solvent, this solvent is intruded between the semiconductor device S and solid immersion lens 1, whereby optical coupling and physical anchoring between the semiconductor device S and solid immersion lens 1 are released.

At this time, the bottom surface portion 3 of the solid immersion lens 1 has been formed in a cylindrical shape and has open faces between the same and semiconductor device S. Therefore, when separating the solid immersion lens 1 from the semiconductor device S, infiltration of the solvent becomes fast, thus separation between the solid immersion lens 1 and semiconductor device S can be carried out in a short time.

In such a manner, by releasing the physical anchoring between the semiconductor device S and solid immersion lens 1 by use of the solvent, the solid immersion lens 1 can be peeled with an extremely weak force, therefore, the semiconductor device S is prevented from being damaged. In addition, since the solid immersion lens 1 can also be prevented from being damaged, it is also possible to utilize the solid immersion lens 1 for a prolonged period of time. Although the solvent has been herein dripped, even by dripping an optical contact liquid, the optical close fitting and physical anchoring between the semiconductor device S and solid immersion lens 1 can be released without damaging the semiconductor device S and solid immersion lens 1.

After an inspection of the inspection point is thus finished, the solid immersion lens 1 is moved to another inspection point or the standby position, whereby the inspection of the inspection point is completed.

As such, in the semiconductor device inspecting method according to the present embodiment, as the solid immersion lens 1, a lens whose bottom surface portion 3 has been formed in a cylindrical shape is used. Therefore, compared to a plano-convex lens, the solid immersion lens 1 can be optically closely fitted and can be removed with respect to the semiconductor device S in a short time. In addition, a high adherence ability can be obtained between the solid immersion lens 1 and semiconductor device S. Furthermore, damage to the semiconductor device S can be prevented.

In the above, a preferred embodiment of the present invention has been described, however, the solid immersion lens according to the present invention is not limited to a solid immersion lens whose bottom surface has a cylindrical shape, and it can employ a mode wherein the bottom surface 3 has been formed in another toroidal shape. Herein, on the X-Y plane of a semiconductor device, when a direction where a curvature in a toroidal shape is increased is set to the Y-direction, it is preferable to set the toroidal shape curvature so that a ratio of a radius of curvature in the X-direction to a radius of curvature in the Y-direction becomes a range of 1:3~1:∞. This is because, if the radius of curvature in the Y-direction is less than three times the radius of curvature in the X-direction, either the physical anchoring degree when the lens is closely fitted to the semiconductor device or optical performance becomes insufficient.

In the above embodiment, the optical contact liquid between the semiconductor device S and solid immersion lens 1 has contained amphipathic molecules, however, as a substitute therefor, a hydrophilic treatment may be applied to the attaching surface of the solid immersion lens 1 to the semiconductor device S.

An improvement in wettability due to the optical contact liquid containing amphipathic molecules is caused by adhesion of hydrophilic groups to the hydrophobic surface. Even in a case where the optical contact liquid does not contain amphipathic molecules, and even when an attaching surface of the solid immersion lens 1 to the semiconductor device S and an attaching surface of the semiconductor device S to the solid immersion lens 1 is hydrophobic, wettability can be improved by applying a hydrophilic treatment to these surfaces. Here, in a case where the surface of the semiconductor device S is originally hydrophilic, this surface can secure wettability without applying a hydrophilic treatment.

Thus, by providing wettability for the respective attaching surfaces of the solid immersion lens 1 and semiconductor device S, similar to the case where an optical contact liquid containing amphipathic molecules is used, an optical contact liquid can be accurately retained at a desirable inspection point on the substrate of the semiconductor device S. In addition, the optical adherence ability between the semiconductor device S and solid immersion lens 1 can be made to a reliable degree without applying an excessive pressure.

As a method for applying a hydrophilic treatment to the solid immersion lens 1 and semiconductor device S, a method of physical adsorption of hydrophilic groups for temporary adhesion exists. As a concrete method for physical adsorption of hydrophilic groups, a method of applying and drying an aqueous solution of amphipathic molecules such as a surfactant, amino acids, and protein before applying a hydrophilic treatment exists. In addition, a method of chemical adsorption of hydrophilic groups for surface reforming also exists as a method for applying a hydrophilic treatment. As the method of chemical adsorption of hydrophilic groups, a method of UV (ultraviolet) light irradiation, a method by wet processing (for example, applying a solution mixing sulfuric acid, hydrogen peroxide, and water), and furthermore, a method by dry processing (for example, irradiating ion beams) and the like exist.

In the above, a preferred example of the present invention has been described, however, the present invention is not limited to the above-described embodiment. For example, although the optical contact liquid containing amphipathic molecules is dripped by an operator in the above-described embodiment, a mode wherein an optical contact liquid dripping unit (an optical coupling material feeding unit for feeding an optical coupling material) is separately provided can also be employed. In addition, a mode wherein an air blower for drying an optical contact liquid, a water-absorbing sheet presser, etc., are provided can also be employed. Furthermore, as a means for wetting a semiconductor device, in addition to the mode of dripping an optical contact liquid, various modes, such as thinly spreading and applying an optical contact liquid, spraying the same, and steaming the same, can also be employed. In this case, since the optical contact liquid swiftly dries, an operation to prompt drying can be omitted.

In addition, a solid immersion lens of the present invention can also be used in a case where an inspection is carried out by, in addition to the semiconductor inspection apparatus shown in the above-described embodiment, an emission microscope using a highly sensitive camera, an OBIRCH analyzer, a time-resolved emission microscope, a heat ray image analyzer or the like. In general, a microscope using the above-described solid immersion lens is a microscope for observing an observed object, which comprises an optical system including an objective lens into which light from the observed object is made incident, for leading an image of the observed object and a solid immersion lens having the above-described structure. In addition, as described above, an image acquisition means for acquiring an image of the observed object (sample) led by the optical system may be provided for the optical system and solid immersion lens.

Next, although examples of the present invention will be described, the present invention is not limited to these examples.

Experiment 1

In Experiment 1, while a solid immersion lens had been optically closely fitted to a semiconductor device, luminance of the semiconductor device during the inspection and separatabiltiy between the solid immersion lens and semiconductor lens after observation were measured. This experiment was carried out for an example where a solid immersion lens 1 as described in the above-described embodiment was employed and for a comparative example where a conventional solid immersion lens was employed. An attaching surface of the conventional solid immersion lens was provided as a plane with a satisfactory surface roughness (plano-convex lens).

Herein, with regard to the solid immersion lens according to the example, a radius of curvature in the X-direction to a radius of curvature in the Y-direction is approximately 1:4.

Figure 6:
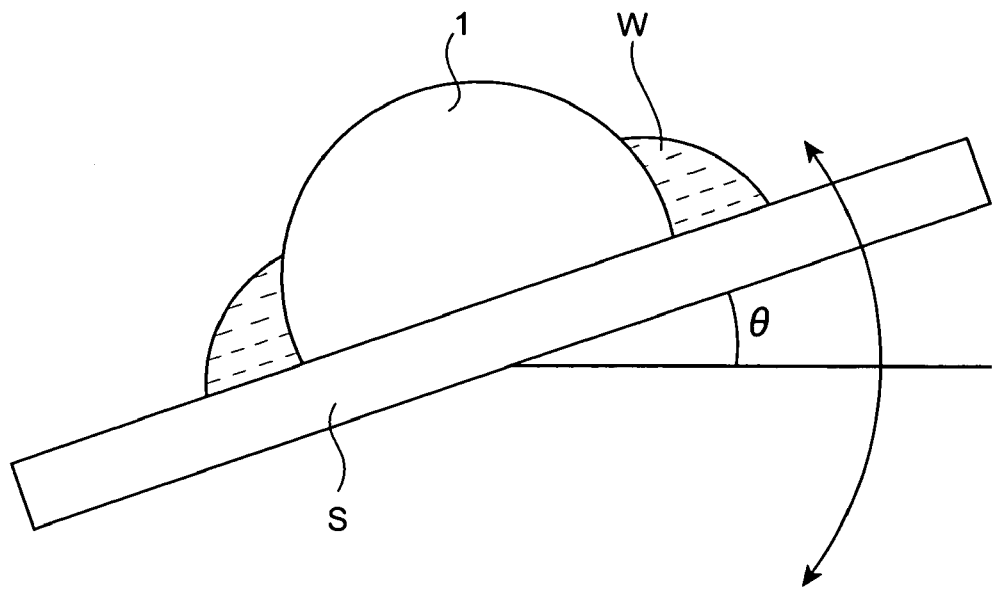
FIG. 6 is a side view showing an implementing condition of an experimentation method of Experiment 1.

As a description of procedures of this experiment, first, the solid immersion lens and semiconductor device were closely fitted via water (hereinafter, referred to as an optical contact liquid) containing a surfactant, and the luminance was measured by the semiconductor inspection apparatus as shown in FIG. 2. Next, after dripping an optical contact liquid W on the part of the semiconductor substrate where the solid immersion lens had been attached, as shown in FIG. 6, the semiconductor device S was moved in a manner inclining the same right and left alternatively in a 2-second cycle at an angle θ nearly equaling 30°, and a time in which the solid immersion lens 1 started to move was measured. This experiment was carried out a plurality of times.

Based on the results of this experiment, a percentage at which the solid immersion lens 1 started to move within 20 seconds after the semiconductor device was started to incline was measured. Results are shown in Table 1.

Experiment 2

In Experiment 2, a physical anchoring degree between the solid immersion lens and semiconductor device was measured. In this experiment, solid immersion lenses according to an example and a comparative example similar to those in Experiment 1 were employed, respectively.

Figure 7:
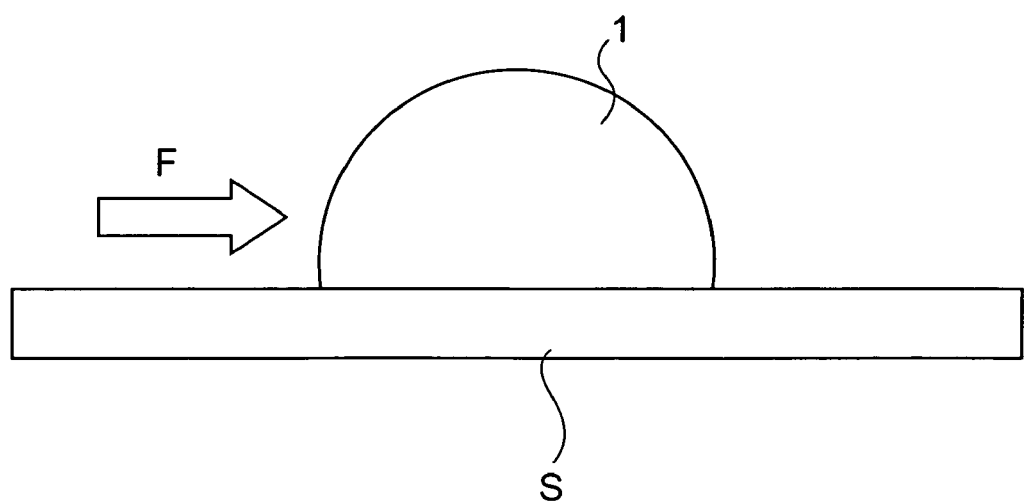
FIG. 7 is a side view showing an implementing condition of an experimentation method of Experiment 2.
Figure 8:
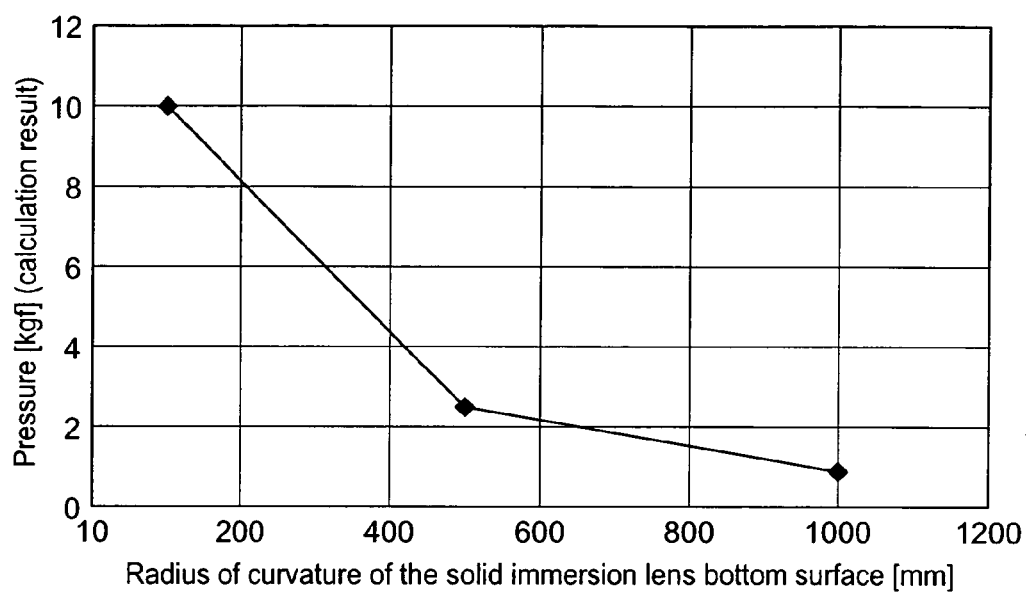
FIG. 8 is a graph showing a relationship between radius of curvature of the bottom surface of a solid immersion lens and pressure required for closely fitting the same to an observed object.

As a description of procedures of this experiment, first, the solid immersion lens and semiconductor device were closely fitted via the above-described optical contact liquid. In this condition, as shown in FIG. 7, the size of a pressure when the solid immersion lens 1 started to move was measured while applying a pressure F to the solid immersion lens 1. This experiment was carried out for an example (solid immersion lens according to the present invention) and a comparative example. The results are shown as adhesion peeling forces in Table 1. Herein, for the comparative example, a solid immersion lens similar to that of Experiment 1 was employed.

TABLE 1

| | Luminance value [A.U.] | Probability of starting to move | Adhesion peeling force |
|---|---|---|---|
| Example | 6 | Approx. 70% | Approx. 30 g-weight |
| Comparative example | 7 | Approx. 20% | Approx. 50 g-weight |

As can be understood from Table 1, the luminance measurements in Experiment 1 show approximately equal luminance values, although the example is slightly inferior to the comparative example. From these results, it was discovered that the example and comparative example do not have a great difference in luminance values when observing a semiconductor device.

In addition, the probability that the solid immersion lens started to move after dripping the optical contact liquid was approximately 70% in the example, whereas in the comparative example, the probability was approximately 20%, showing a very low result. From these results, it was discovered that, when a solid immersion lens is separated from a semiconductor device after an observation, the solid immersion lens can much more easily be separated in the example than in the comparative example.

Furthermore, when a force was applied to the solid immersion lens closely fitted to the semiconductor device, the solid immersion lens according to the present embodiment started to move by a force of approximately 30 g weight, whereas in the comparative example, the solid immersion lens started to move by a force of approximately 50 g weight. In the prior art, since the close fitting area between the solid immersion lens and semiconductor device is great, the adhesion peeling force is strong, however, in comparison with the comparative example, the example is not greatly inferior in the adhesion peeling force.

A further description will be given of a solid immersion lens according to the present invention.

It has been known that, in a solid immersion lens (SIL), on the above-described hemispherical or hyperhemispherical construction and a sample observing surface set according thereto, aplanatic image formation producing no spherical aberration and coma aberration is obtained. However, with such an SIL construction and usage conditions, the position where aberrations are eliminated exists at only one point in either case, and accordingly, application of SILs has been limited to optical pickups and the like.

Namely, on the sample observing surface used in the SIL, image plane characteristics are unsatisfactory when an observation of a sample is intended in a wide range. Therefore, in an attempt to observe a sample image by use of an SIL, problems have existed in an obtained image such as in a limit field of view available for the observation, such that resolution of an obtained image is lowered at its peripheral portion compared to the central portion, and the periphery or the vicinity of the center cannot be viewed under the influence of a curvature of field.

To cope therewith, it is preferable that a solid immersion lens is formed of a material with a refractive index $n_L$ while having a spherical optical surface with a radius of curvature $R_L$, and is constructed so that a distance along the optical axis from the vertex to a virtual observing surface when the refractive index of an observed object (sample) is equal to a refractive index $n_L$ is provided, by a coefficient k (0<k<1) set so that geometrical aberration characteristics satisfy predetermined conditions, as $L=R_L+k\times(R_L/n_L)$, and where the refractive index of an observed object (sample) is provided as $n_s$ and the thickness of an observed object (sample) to an actual observing surface is provided as $t_s$, a thickness along the optical axis satisfies $d_L=L-t_s\times(n_L/n_s)$.

In the above-described solid immersion lens, a lens shape is set by using a coefficient k set by evaluating geometrical aberration characteristics as a result of a solid immersion lens and also taking the reflective index $n_s$ and thickness $t_s$ of a sample such as a substrate to be an observed object into consideration. Thereby, as described above, while widening a field of view available for an observation, it becomes possible to satisfactorily observe a desirable observing part of the sample.

In particular, by providing a solid immersion lens by combining the above-described construction wherein an attaching surface to a sample is formed in a toroidal shape with the construction wherein a lens shape is set by using a coefficient k set by evaluating geometrical aberration characteristics and also taking the refractive index $n_s$ and thickness $t_s$ of a sample such as a substrate to be an observed object into consideration, a light flux with a high NA can be passed, positional control of a solid immersion lens when optically coupling the same with a sample is simplified, and while widening a field of view available for an observation, a solid immersion lens whereby satisfactorily observing a desirable observing part of a sample becomes possible is realized. Here, in a solid immersion lens whose attaching surface has a toroidal shape as described above, a thickness $d_L$ along an optical axis Ax of the solid immersion lens equals a distance from the vertex of the solid immersion lens to the sample-side lens surface (a part where the solid immersion lens and the sample are most proximate).

In the aforementioned solid immersion lens, the coefficient k is preferably a value within a range of 0.5<k<0.7. At this time, an observation with a condition where image plane characteristics through a solid immersion lens become substantially flat becomes possible.

Or, the coefficient k is preferably a value within a range of $0<k\leq0.5$. At this time, an observation with a condition where chromatic aberration and spherical aberration through a solid immersion lens have substantially been reduced becomes possible.

In addition, in terms of a sample observation method using a solid immersion lens, it is preferable, by use of a solid immersion lens formed of a material with a refractive index $n_L$ while having a spherical optical surface with a radius of curvature $R_L$, by employing, based on a coefficient k ($0<k<1$) set so that geometrical aberration characteristics through the solid immersion lens satisfy predetermined conditions, a surface which contains a point positioned on the downstream side by $k\times(R_L/n_L)$ along the optical axis from the sphere center of the optical surface and is approximately orthogonal to the optical axis as a sample observing surface, to carry out an observation of a sample (observed object) by use of a solid immersion lens.

In the above-described sample observation method, without employing a construction corresponding to a hemispherical form wherein a surface including the sphere center is employed as a sample observing surface or a construction corresponding to a hyperhemispherical form wherein a surface including a point positioned on the downstream side by $(R_L/n_L)$ along the optical axis from the sphere center as a sample observing surface, a coefficient k is set by evaluating geometrical aberration characteristics through a solid immersion lens. And, by employing a surface including a point determined by this coefficient k as a sample observing surface, a sample observation is carried out. Thereby, while widening a field of view available for an observation, it becomes possible to satisfactorily observe an image of the sample by use of a solid immersion lens.

Herein, for the evaluation of geometrical aberration characteristics through a solid immersion lens, it is preferable to evaluate geometrical aberration characteristics by use of a virtual optical system using a rear-side focal plane of the solid immersion lens as a pupil plane and to set a coefficient k based on the evaluation result. Thereby, an object-side telecentricity can be provided by setting a pupil plane to the rear-side focal plane of the solid immersion lens, thus a form to meet an actual reflected light observation by laser scanning, etc., can be provided. In a case where the solid immersion lens is used in combination with an actual microscope, the pupil position of the microscope objective lens no longer has a function as a pupil, and the pupil of the optical system including the solid immersion lens is at a rear-side focal position of the solid immersion lens.

In addition, it is preferable to evaluate geometrical aberration characteristics through a solid immersion lens in terms of a sagittal image plane, a meridional image plane, or an average image plane between the sagittal image plane and meridional image plane and set a coefficient k based on the evaluation result. Thereby, geometrical aberration characteristics on a sample observing surface through a solid immersion lens can satisfactorily be set.

In addition, in the above-described sample observation method, it is also satisfactory that the solid immersion lens has a thickness of $d_L=R_L+k\times(R_L/n_L)$ along the optical axis and the sample observing surface is coincident with a sample-side lens surface of the solid immersion lens. Or, it is also satisfactory that the solid immersion lens has a thickness of $d_L<R_L+k\times(R_L/n_L)$ along the optical axis, the sample observing surface is a virtual observing surface when the refractive index of a sample is equal to a refractive index $n_L$ of the solid immersion lens, and where the refractive index of a sample is provided as $n_s$ and the thickness of a sample to an actual observing surface is provided as $t_s$, the thickness of the solid immersion lens satisfies $d_L=L-t_s\times(n_L/n_s)$ compared with a distance along the optical axis from the vertex to the virtual observing surface of $L=R_L+k\times(R_L/n_L)$.

First, an outline of a solid immersion lens (SIL) of the present invention and a sample observation method using the same will be described together with a construction and usage conditions of a conventionally used SIL. Here, in the following, although a description will be given mainly of setting of a thickness along the optical axis of the SIL, a toroidal shape of an attaching surface of the SIL to a sample (observed object), an effect thereof, and the definition of an SIL thickness when the attaching surface has a toroidal shape are as described above.

Figure 9:
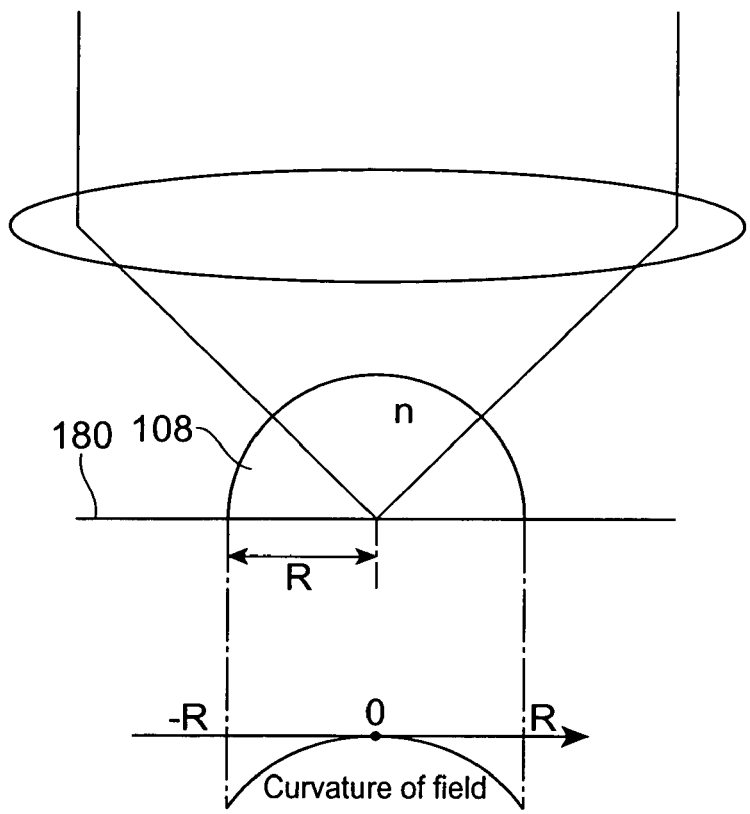
FIG. 9 is a view showing an example of a construction and usage conditions of a conventional solid immersion lens.

FIG. 9 is a view showing an example of a construction and usage conditions of a conventional SIL. An SIL 108 shown in FIG. 9 is a lens having a hemispherical form with a refractive index n and a radius of curvature R. In such an SIL 108, the sphere center is a focal point, and a surface including the sphere center is set to a sample observing surface 180. In addition, the numerical aperture NA and magnification for a sample observation both become n times. When image plane characteristics of the SIL 108 are considered in such a construction, as shown in FIG. 9, a curvature of field occurs, wherein the image plane is shifted to the downstream side as it becomes distant from the focal point.

Figure 10:
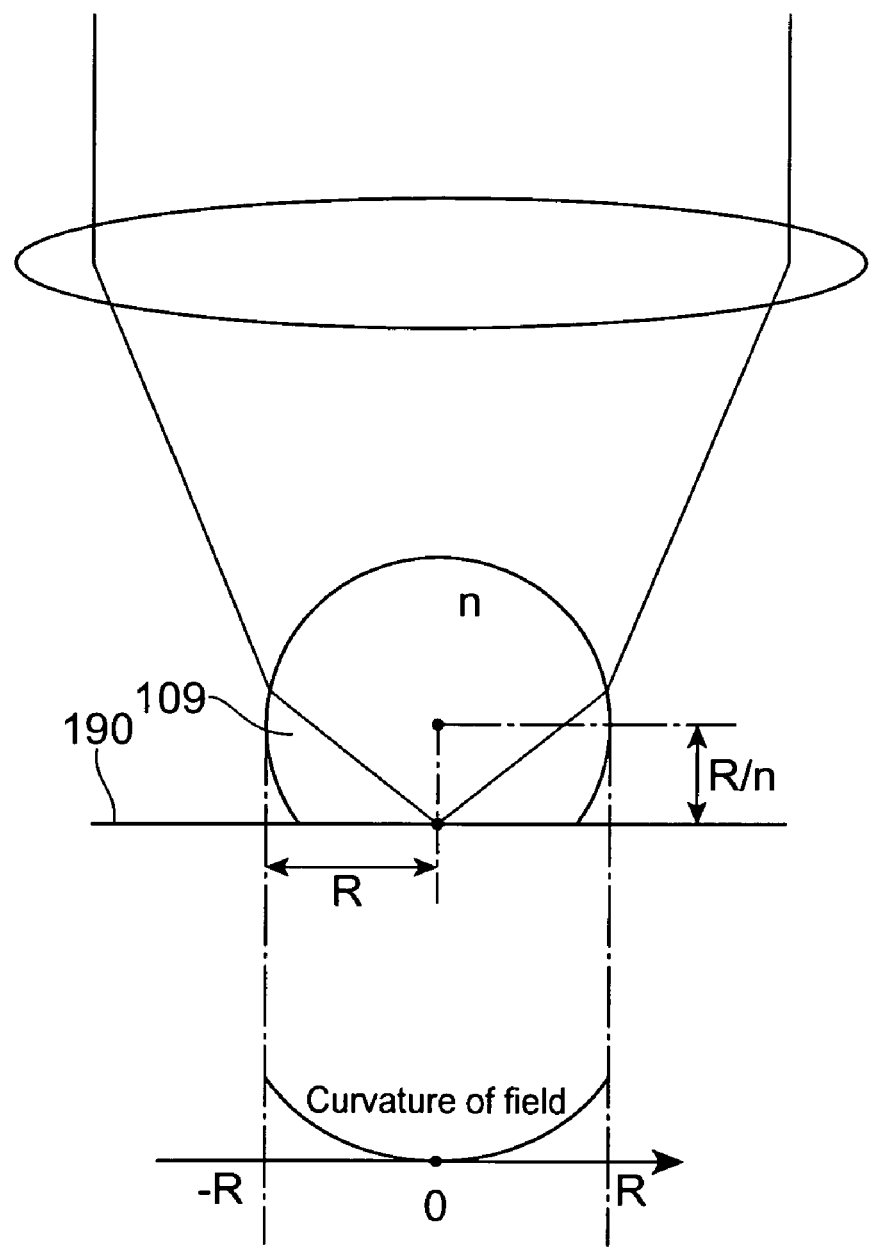
FIG. 10 is a view showing another example of a construction and usage conditions of a conventional solid immersion lens.

FIG. 10 is a view showing another example of a construction and usage conditions of a conventional SIL. An SIL 109 shown in FIG. 10 is a lens having a hyperhemispherical form with a refractive index n and a radius of curvature R. In such an SIL 109, a point positioned on the downstream side by R/n along the optical axis from the sphere center is a focal point, and a surface including the point is set to a sample observing surface 190. In addition, the numerical aperture NA and magnification for a sample observation both become $n^2$ times. When image plane characteristics of the SIL 109 are considered in such a construction, as shown in FIG. 10, a curvature of field in a direction opposite to that of FIG. 9 occurs, wherein the image plane is shifted to the upstream side as it becomes distant from the focal point.

As a result of a detailed examination of such an occurrence of a curvature of field in a sample observation using an SIL, the inventor of the present invention has discovered that, between the sphere center provided as a focal point in the above-described construction and the point positioned on the downstream side by R/n along the optical axis from the sphere center, the magnification changes between n times and $n^2$ times and the curvature of field thereof also changes between the curvatures of field of opposite directions shown in FIG. 9 and FIG. 10. The sample observation method using an SIL of the present invention is, based on such discovery, for carrying out an observation of a sample image by use of an SIL with a construction and usage conditions suitable for imaging.

Figure 11:
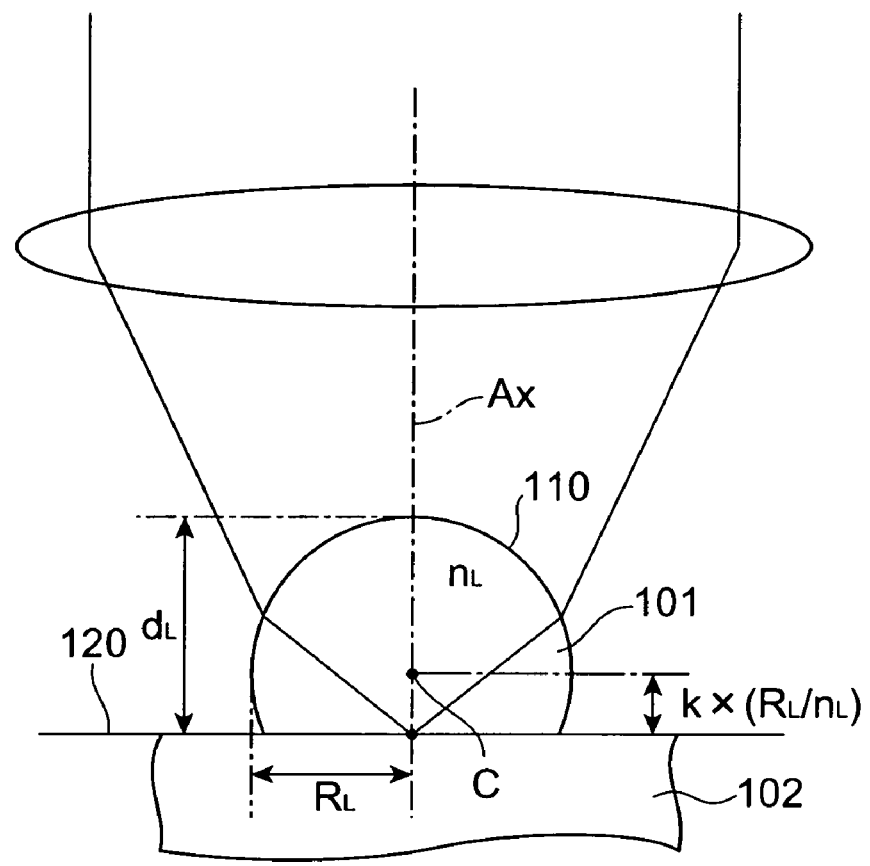
FIG. 11 is a view showing a construction and usage conditions of a solid immersion lens to be used in a sample observation method of the present invention.

FIG. 11 is a view showing a sample observation method of the present invention and a construction and usage conditions of an embodiment of a solid immersion lens to be used therein. In the present sample observation method, for a sample 102 to be an observed object, as a lens to enlarge a light image from the sample 102, an SIL 101 formed of a material with a refractive index $n_L$ is used. This SIL 101 is formed while employing, as its lens surface, an optical surface 110 with a spherical form with a radius of curvature $R_L$ having an axis Ax as its optical axis and a point C as its sphere center.

In a sample observation using such an SIL 101, a point positioned on the downstream side by $k \times (R_L/n_L)$ along the optical axis Ax from the sphere center C of a spherical lens surface 110 is used as a focal point. Then, while using a surface 120 which includes this focal point and is approximately orthogonal to the optical axis Ax as a sample observing surface, an observation of the sample using the SIL 101 is carried out.

Herein, the above-described coefficient k which determines a focal point through the SIL 101 and a position of the sample observing surface 120 viewed from the sphere center C is a coefficient set within a range of $0 < k < 1$. Accordingly, this focal point position is a position between the sphere center C and point positioned on the downstream side by $R_L/n_L$ along the optical axis from the sphere center C. In particular, this coefficient k is set so that the geometrical aberration characteristics through the SIL 101 satisfy predetermined conditions.

Namely, as described above, between the sphere center C and point positioned on the downstream side by $R_L/n_L$ along the optical axis Ax from the sphere center C, the magnification and curvature of field change in sequence. Compared with such changes in characteristics, geometrical aberration characteristics through the SIL 101 and changes thereof, etc., are evaluated, and based on the evaluation result, setting of an appropriate coefficient k and selection of a focal point thereby are carried out. And, while using a surface including the point determined by the coefficient k as a sample observing surface 120, an image of the sample 102 is observed. At this time, the SIL 101 can be used with a condition where the curvature of field has been reduced and aberration degradation has been sufficiently suppressed. Thereby, while widening a field of view available for an observation, it becomes possible to satisfactorily observe an image of the sample 102 by use of the SIL 101.

Here, in the example shown in FIG. 11, the sample observing surface 120 determined by the coefficient k is coincident with a plane-formed lens surface of the SIL 101 positioned on the sample 102 side. Also, at this time, a distance from the vertex of the SIL 101 to the lens surface of the sample 102 side, namely, a thickness along the optical axis Ax of the SIL 101 is $d_L = R_L + k \times (R_L/n_L)$.

Figure 12:
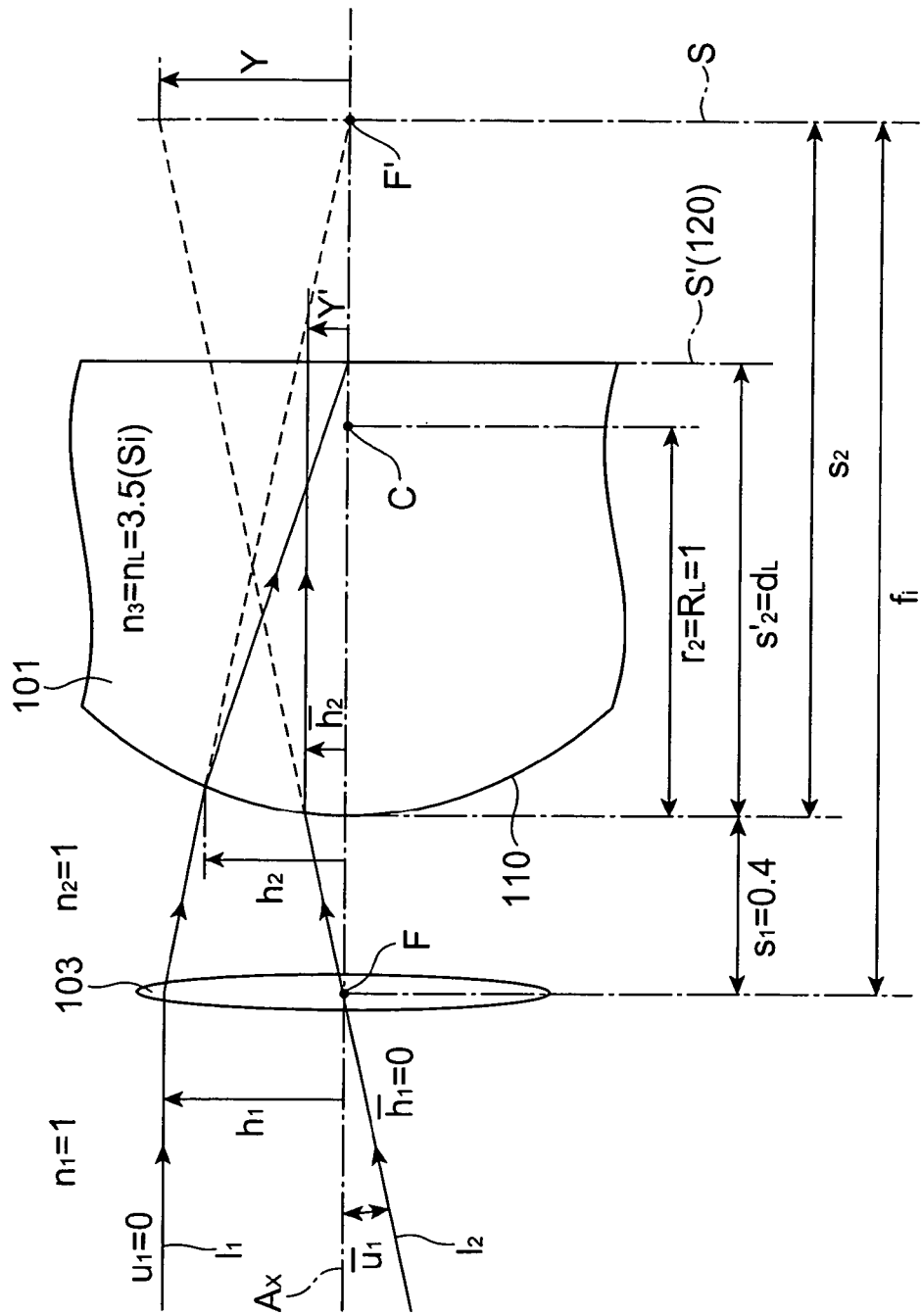
FIG. 12 is a view showing a virtual optical system used to evaluate geometrical aberration characteristics and chromatic aberration characteristics through the solid immersion lens shown in FIG. 11.
Figure 13:
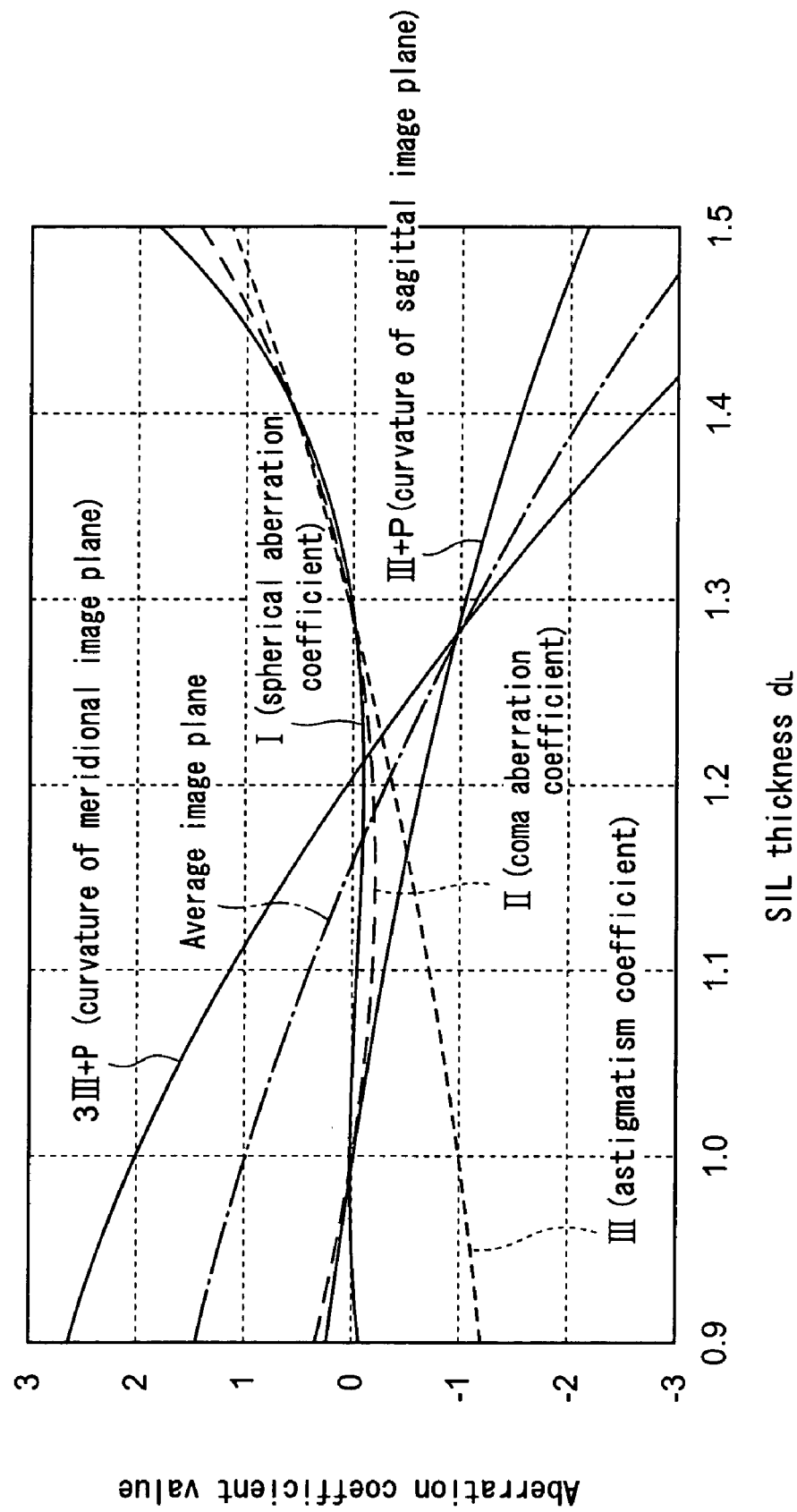
FIG. 13 is a graph showing solid immersion lens characteristics evaluated by use of the virtual optical system shown in FIG. 12.

Hereinafter, a method for evaluating aberrations and image plane characteristics in a sample image observation by use of the SIL 101, a preferred construction and usage conditions of the SIL 101 will be described in detail by use of FIG. 12 and FIG. 13. FIG. 12 is a view showing a virtual optical system used to evaluate geometrical aberration characteristics and chromatic aberration characteristics through the SIL shown in FIG. 11. FIG. 13 is a graph showing SIL characteristics evaluated by use of the virtual optical system shown in FIG. 12.

Here, in FIG. 12, n denotes a refractive index, s denotes a distance from the object plane to the principal plane, and h denotes a light ray height. In addition, the superscript bar shows an amount related to the principal light ray. However, in the specification, "$h_1$" with a superscript bar is noted as "$\bar{h}_1$", for example.

First, a virtual optical system to evaluate image plane characteristics through an SIL will be described. Herein, as shown in FIG. 12, silicon (Si) is assumed as a material of the SIL 101, and a refractive index thereof is provided as $n_3 = n_L = 3.5$. In addition, for regions other than the inside of the SIL 101 with a refractive index $n_3$, a refractive index is provided as $n_1 = n_2 = 1$. In addition, for the lens surface 110 formed in a spherical form centered on the sphere center C, a radius of curvature thereof is provided as $r_2 = R_L = 1$.

For such an SIL 101, for an evaluation of aberrations and image plane characteristics thereof, a virtual optical system using a back focal plane of the SIL 101 as a pupil plane is introduced. Concretely, as shown in FIG. 12, a virtual objective lens 103 having no aberration is introduced and disposed at a back focal point F of the SIL 101. A distance $s_1$ between the surface vertex of the lens surface 110 of the SIL 101 and back focal point F is determined by $s_1 = r_2/(n_3 - n_2)$, and in the above-described example with $n_3 = 3.5$, the distance results in $s_1 = 0.4 \times R_L = 0.4$.

In addition, a focal length of this aberration-free virtual objective lens 103 is provided as fi, and a front-side focal position is provided as F'. A thickness $s_2'$ of the SIL 1 is provided as a distance from a focal position where a light emerged from the virtual objective lens 103 with $u_1 = 0$ and $h_1$ is focused through the lens surface 110 to the surface vertex of the lens surface 110. By evaluating the SIL 101 by use of a virtual optical system into which such a virtual objective lens 103 has been introduced, an entrance pupil of the entire optical system is set on the virtual objective lens 103 positioned distant by $s_1 = 0.4 \times R_L$ from the lens surface 110. In addition, by setting the entrance pupil, etc., as such, telecentricity is obtained inside the SIL 101, thus a form to meet an actual observation system such as a reflected light observation by laser scanning can be provided. Thereby, aberrations and image plane characteristics through the SIL 101 can appropriately be evaluated.

In FIG. 12, together with the above-described optical system construction of the SIL 101 and virtual objective lens 103, two light rays $l_1$ and $l_2$ are illustrated. Of these, the light ray $l_1$ has an angle formed with the optical axis Ax of $u_1 = 0$, a light ray height of $h_1$ at the virtual objective lens 103, and a light ray height of $h_2$ at the lens surface 110 of the SIL 101 and becomes a light ray parallel to the optical axis Ax on the upstream side more than the virtual objective lens 103. In addition, this light ray $l_1$ passes through a point on the optical axis Ax in a surface S' corresponding to the sample observing surface 120. Moreover, with regard to the light ray $l_1$, a light ray shown by a dotted line when the SIL 101 does not exist passes through a point F' on the optical axis Ax in a focal plane S through the virtual objective lens 103.

In addition, the light ray $l_2$ has an angle formed with the optical axis Ax of $u_1$, a light ray height of $h_1 = 0$ at the virtual objective lens 103, and a light ray height of $h_2$ at the lens surface 110 of the SIL 1 and becomes a light ray parallel to the optical axis Ax on the downstream side more than the lens surface 110. In addition, this light ray $l_2$ passes through a point F on the optical axis Ax in the virtual objective lens 103 and has, in the sample observing surface S', a distance Y' from the optical axis Ax. Moreover, with regard to the light ray $l_2$, a light ray shown by a dotted line when the SIL 101 does not exist has, in the focal plane S, a distance Y from the optical axis Ax.

In addition, a distance from the surface vertex of the lens surface 110 of the SIL 101 to the focal plane S is provided as $s_2$, a distance to the sample observing surface S', namely, a thickness of the SIL 101 is provided as $s_2' = d_L$. In the virtual optical system of FIG. 12 having the above construction and conditions, when aberration coefficients of spherical aberration coefficient I, coma aberration coefficient II, astigmatism coefficient III, Petzval sum P, curvature of a sagittal image plane III+P, and curvature of a meridional image plane 3III+P of the SIL 101 are expressed by the thickness $d_L$ of the SIL 101, these can be determined as in the following expressions (1)-(6), respectively.

$$I = h_2^4 \cdot Q_2^2 \cdot \Delta(1/n_L s)_2 = (d_L/1.4)^4 \cdot \{4.9(d_L-1)/d_L\}^2 \cdot (3.5 - 4.5/d_L) = 6.25(d_L-1)^2(3.5d_L - 4.5)d_L \qquad (1)$$

$$II = J_2 \cdot I = 2.5(d_L - 1)(3.5d_L - 4.5)d_L \quad (2)$$

$$III = J_2 \cdot II = (3.5d_L - 4.5)d_L \quad (3)$$

$$P = p = (1/n_2 - 1/n_3)/r_2 = 1 \quad (4)$$

$$III + P = 1 + (3.5d_L - 4.5)d_L \quad (5)$$

$$3III + P = 1 + 3(3.5d_L - 4.5)d_L \quad (6)$$

Herein, $Q_2$ means Abbe's invariant. In addition, $Q_2$ and $J_2$ are expressed by the following expressions.

$$Q_2 = n_2(1/r_2 - 1/s_2) = 4.9(d_L - 1)/d_L$$

$$J_2 = \overline{Q_2} \overline{h_2} / Q_2 h_2$$

In addition, curvatures (actual sizes) of a Petzval image plane, a sagittal image plane, and a meridional image plane become as in the following, respectively.

$$-P/fi = -0.7143 \text{ (1/mm)} = \text{Fixed} \ldots \text{Petzval image plane}$$

$$-\{1 + (3.5d_L - 4.5)d_L\}/1.4 \text{ (1/mm)} \ldots \text{Sagittal image plane}$$

$$-\{1 + 3(3.5d_L - 4.5)d_L\}/1.4 \text{ (1/mm)} \ldots \text{Meridional image plane}$$

FIG. 13 shows a graph of the respective aberration coefficients of spherical aberration coefficient I, coma aberration coefficient II, astigmatism coefficient III, curvature of a sagittal image plane III+P, and curvature of a meridional image plane 3III+P determined by the above-described expressions and an average image plane between the sagittal image plane and meridional image plane. In this graph, the horizontal axis shows SIL thickness $s_2' = d_L$, and the vertical axis shows values of the respective aberration coefficients. Moreover, the thickness $d_L$ shown in this horizontal axis and the coefficient k shown in FIG. 11 has, since $R_L = 1$ in FIG. 12, a relationship of $k = n_L \times (d_L - 1) = 3.5 \times (d_L - 1)$.

According to the respective plotted graph shown in FIG. 13, at a point of $d_L = R_L = 1$ corresponding to a case where a surface including the sphere center is provided as a sample observing surface (see FIG. 9) and a point of $d_L = R_L + R_L/n_L = 1.286$ corresponding to a case where a surface including a point positioned on the downstream side by $R_L/n_L$ along the optical axis from the sphere center is provided as a sample observing surface (see FIG. 10), respectively, the spherical aberration coefficient I and coma aberration coefficient II are both zero and thus satisfy aplanatic conditions. However, at these points, respectively, a curvature of field occurs as mentioned above. Here, at a point of $d_L = 1$, the curvature of a sagittal image plane III+P is also zero. In addition, at a point of $d_L = 1.286$, the astigmatism coefficient III is also zero.

In comparison therewith, in terms of the average image plane between the sagittal image plane and meridional image plane, it can be understood that the image plane is flat at a point of $d_L = R_L + k(R_L/n_L) = 1.163 \times R_L = 1.163$. Namely, in order to satisfy a condition where the average image plane becomes a plane vertical to the optical axis, which is a condition where the image plane is flat and a wide field of view can be secured, it is satisfactory that the curvature of an image plane becomes III+P=−(3III+P). Based on this condition, $d_L = 1.163$ is obtained from the above-described respective expressions. Also, at this time, the coefficient k set for the sample observing surface is determined as approximately 0.6 (k=0.57). By carrying out a sample observation by use of the SIL 101 with a construction and usage conditions to which the coefficient k thus obtained has been applied, it becomes possible to obtain a satisfactory sample image with a wide field of view.

Here, in a case where a calculation is carried out with a condition of a normal entrance pupil position where telecentricity is obtained outside the SIL, the average image plane is flattened at a point with an SIL thickness of $1.274 \times R_L$, thus showing a calculation result completely different from the above-described result.

A solid immersion lens of the present invention and a sample observation method using the same are not limited to those in the above-described embodiments, and various modifications can be made. For example, although, in the above-described example, silicon has been mentioned as an example of the SIL material, in addition to silicon, various materials may be used depending on the material of an applying sample and observational conditions, etc.

In addition, in the above-described example, the refractive index of the SIL is provided as 3.5=fixed. This corresponds to a case of a sample observation with a single wavelength or a case where a change in the refractive index with a wavelength change can be disregarded. Accordingly, the condition where k is provided in the vicinity of 0.6 as in the above is effective in carrying out an observation, inspection and the like for a sample by a light with a single wavelength.

In contrast thereto, in an emission observation or the like where a wavelength width for an observation is wide such as, for example, a case where an observation is carried out with a wavelength width of 750 nm-1050 nm, for an SIL made of silicon, by providing k on the order of 0.3, chromatic aberration and other aberrations are balanced. As such, it is preferable to carry out an evaluation of image plane characteristics and setting of a coefficient k, etc., while taking a wavelength width to carry out an observation into consideration, if necessary.

In addition, with regard to the coefficient k, a coefficient k is set by a point where the average image plane is flattened in the above-described example. Thereby, image plane characteristics on the sample observing surface through the SIL can satisfactorily be set. However, for this setting of a coefficient k, a method of setting by a point within a predetermined condition range in the vicinity of a point where the average image plane is flattened may be employed. Or, a coefficient k may be set by a point where not the average image plane but the sagittal image plane or meridional image plane is flattened.

Figure 14:
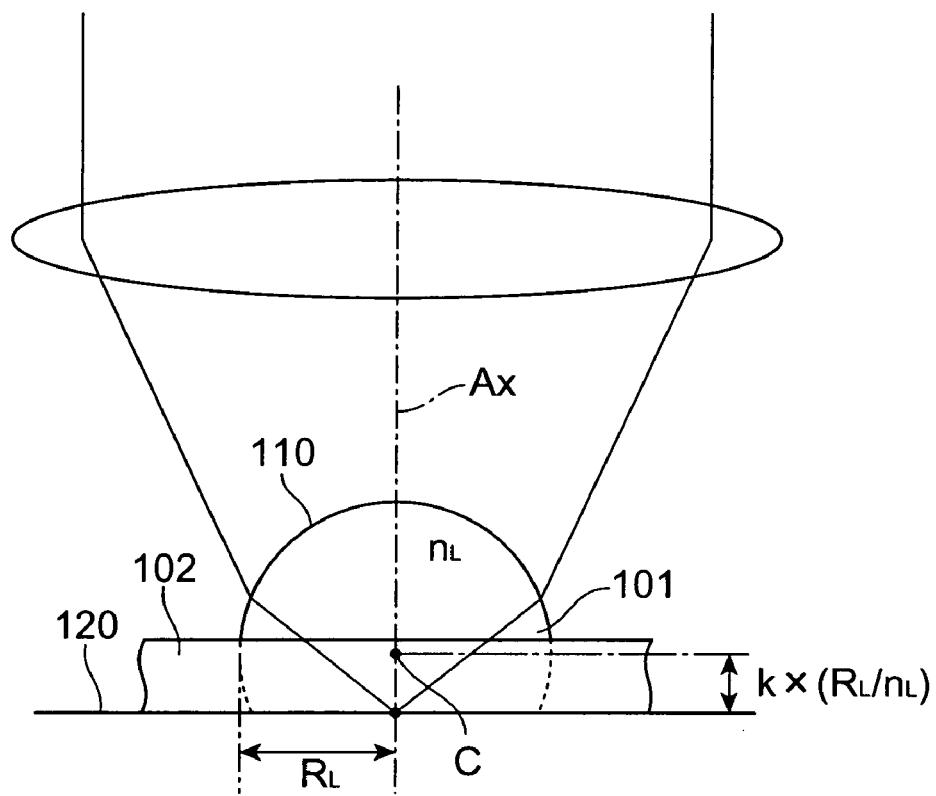
FIG. 14 is a view showing another example of a construction and usage conditions of a solid immersion lens used in a sample observation method of the present invention.

In addition, with regard to a method for installing an SIL with respect to a sample, although a construction where the surface of the sample 102 is the sample observing surface 120 has been shown in FIG. 11, the invention is not limited to such a construction. FIG. 14 is a view showing another example of a construction and usage conditions of a solid immersion lens used in a sample observation method of the present invention. In this example, to the silicon substrate 102, which is a sample, the SIL 101 similarly made of silicon is applied, and the rear surface of the substrate 102 is the sample observing surface 120.

In such a construction, by functioning of a predetermined part of the silicon substrate 102 as a downstream-side part of the SIL 101, a sample image can be observed similarly to the case where the front surface is provided as a sample observing surface 120. Such an observing method can be applied to a case where a semiconductor device is inspected by a rear-surface observation, for example.

A solid immersion lens of the present invention and a sample observation method using the same will further be described.

Figure 15:
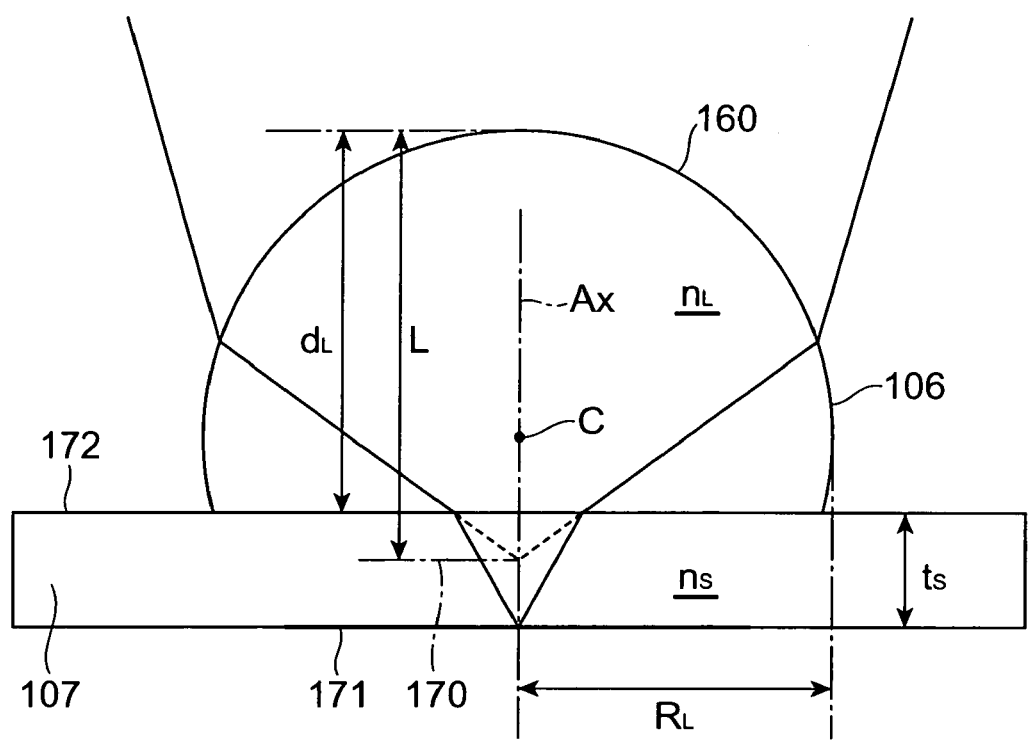
FIG. 15 is a view showing another embodiment of a solid immersion lens and a sample observation method of the present invention.

FIG. 15 is a view showing another embodiment of a solid immersion lens and a sample observation method of the present invention. In the present sample observation method, for a sample 107 (for example, a semiconductor device) to be an observed object, an SIL 106 formed of a material with a refractive index $n_L$ is used as a lens to enlarge a light image from the sample 107. This SIL 106 is formed while employing a spherical optical surface 160 with a radius of curvature $R_L$ having an axis Ax as its optical axis and a point C as its sphere center as a lens surface. Here, in the present embodiment as well, setting of a coefficient k is similar to that of the embodiment of FIG. 11.

In FIG. 15, in the sample 107, its surface on the side opposite the SIL 106 is provided as an observing surface 171 (for example, a device surface of a semiconductor device). In addition, with respect to this sample 107, the SIL 106 is disposed so that its sample 107-side, plane-formed lens surface is brought into close contact with a rear surface 172 of the sample 107. Here, a refractive index of the sample 107 is provided as $n_s$, and a thickness of the sample 107 is provided as $t_s$. This thickness $t_s$ is a thickness of the sample 107 along the optical axis Ax from the rear surface 172 to the observing surface 171, which is an actual observing surface through the SIL 106.

In such a construction, for focusing on the observing surface 171 of the sample 107, a thickness of the SIL 106 along the optical axis Ax is $d_L = R_L + k \times (R_L/n_L)$. In addition, a sample observing surface 170 (0<k<1), which includes a point positioned on the downstream side by $k \times (R_L/n_L)$ along the optical axis Ax from the sphere center C of the lens surface 160 and is approximately orthogonal to the optical axis Ax as mentioned above with regard to FIG. 11, is a virtual observing surface (an apparent observing surface determined by a lens shape of the SIL 106) when a refractive index of the sample 107 is equal to the refractive index $n_L$ of the SIL 106.

Herein, a distance from the vertex of the SIL 106 to the virtual observing surface 170 along the optical axis Ax is provided as $L = R_L + k \times (R_L/n_L)$ as shown in FIG. 15. This distance L corresponds to a focal length determined from a shape of the lens surface 160 of the SIL 106. In addition, at this time, the thickness of the SIL 106 has been set so as to satisfy $d_L = L - t_s \times (n_L/n_s)$. Here, in FIG. 15, a light path which passes through the SIL 106 and sample 107 and converges onto the actual observing surface 171 is shown by a solid line. In addition, a light path which converges onto the virtual observing surface 170 in a case where the refractive index of the sample 107 is assumed to be equal to that of the SIL 106 is shown by a dotted line.

In the SIL 106 with a thickness of $d_L = L - t_s \times (n_L/n_s)$ according to the present embodiment and the sample observation method using the same, the coefficient k set by evaluating geometrical aberration characteristics through SIL 106 is used, and while taking the refractive index $n_s$ and thickness $t_s$ of the sample 107 to be an observed object into consideration, the lens shape of the SIL 106 is set. Thereby, as described above, while widening a field of view available for an observation, it becomes possible to satisfactorily observe a desirable observing part of the sample 107. Herein, selection of a coefficient k is similar to that of the embodiment shown in FIG. 11. In addition, with regard to the thickness $t_s$, the thickness $t_s$ of the sample 107 is directly used since the surface of the sample 107 on the side opposite the SIL 106 is the observing surface 171 in FIG. 15, however, in a case where an observing surface is set inside the sample 107, it is satisfactory to provide a thickness of the sample to the observing surface as $t_s$.

Figure 16:
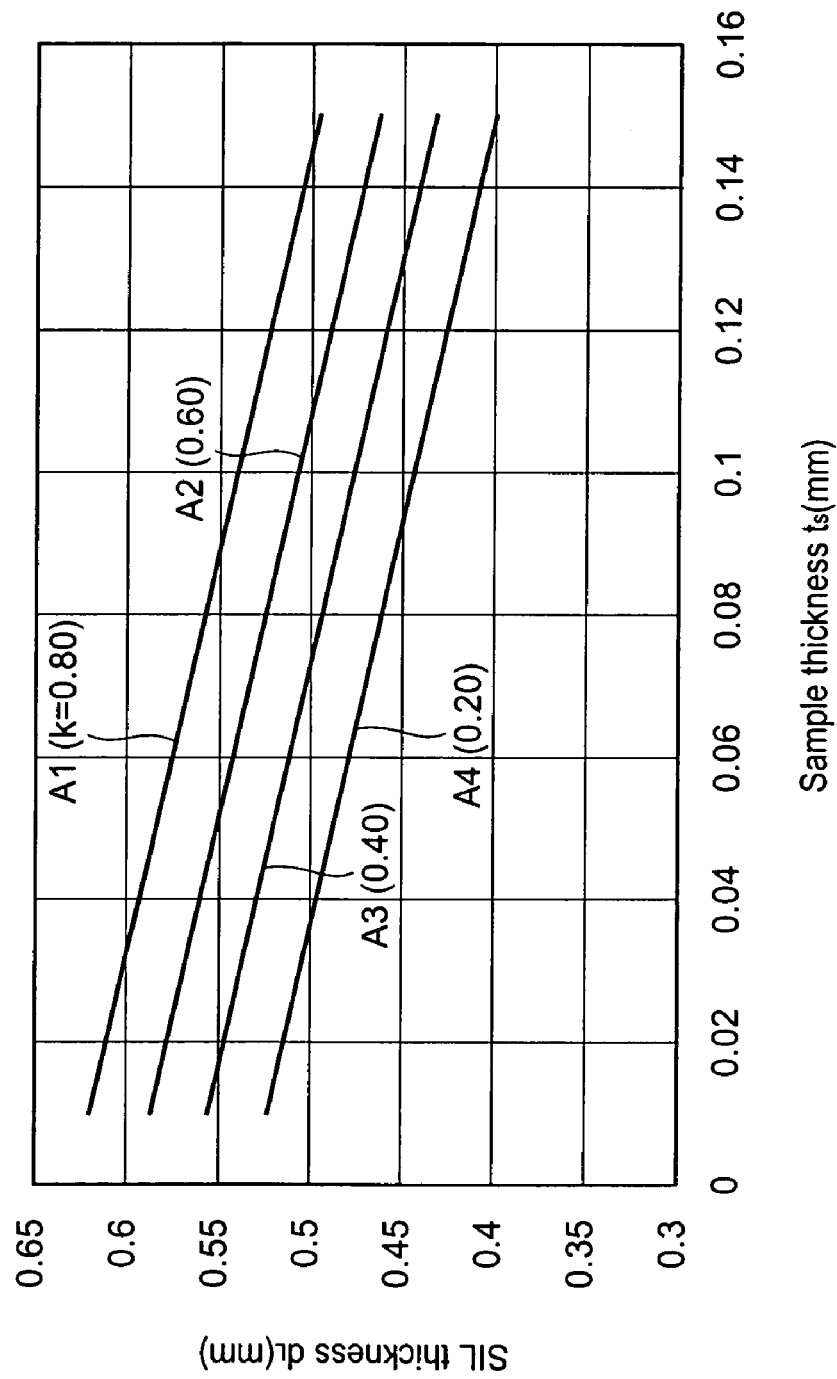
FIG. 16 is a graph showing an example of correlation between the sample thickness and SIL thickness.

FIG. 16 is a graph showing an example of correlation between the sample thickness and SIL thickness. In this graph, the horizontal axis shows a thickness $t_s$ (mm) of the sample 107, and the vertical axis shows a thickness $d_L$ (mm) of the SIL 106. In this graph, a refractive index of the SIL 106 is provided as $n_L = 3.1$ (material GaP), a refractive index of the sample 107 is provided as $n_s = 3.5$ (material Si), and a radius of curvature of the SIL 106 is provided as $R_L = 0.5$ mm. In addition, the plotted graph A1 shows a correlation when a coefficient k=0.80, and A2, k=0.60, and A3, k=0.40, and A4, k=0.20. The thickness $d_L$ of the SIL 106 is set as in the examples shown in the graph of FIG. 16 according to the respective materials and coefficient k values, etc.

Next, setting of a coefficient k in the above-described solid immersion lens and sample observation method will be examined. In general, if a demand for securing a wide field of view exists, it is preferable that the coefficient k is within a range of 0.5<k<0.7, as in the above-described example of k=0.6. At this time, an observation with a condition where image plane characteristics through a solid immersion lens become substantially flat becomes possible. For example, in a case of an observation using a laser light from a monochromatic laser, there is no problem of chromatic aberration, and a coefficient k can be set to widen the field of view.

On the other hand, in a case where spherical aberration and chromatic aberration in a solid immersion lens must be considered, it is preferable that the coefficient k has a value within 0<k≦0.5 as in the above described example of k=0.3. At this time, an observation with a condition where spherical aberration and chromatic aberration through the solid immersion lens have been substantially reduced becomes possible. Such a preferred range of the coefficient k is similar in either case of the construction shown in FIG. 11 and construction shown in FIG. 15.

Figure 17A:
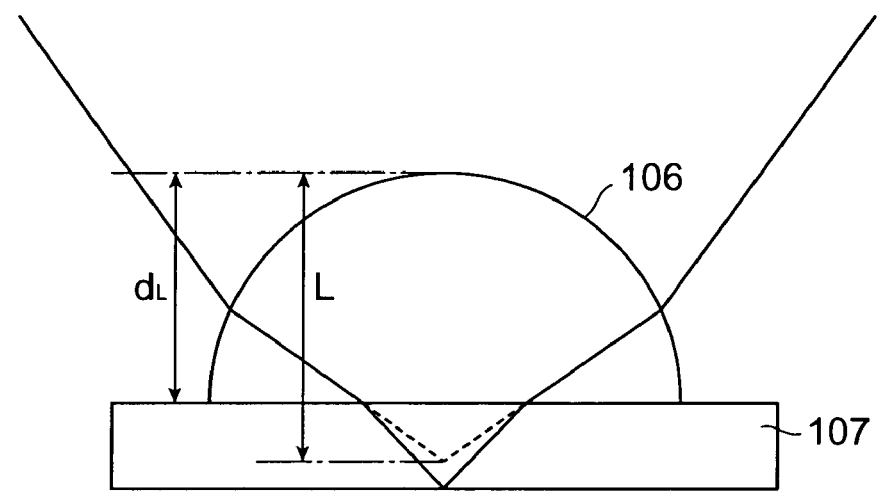
FIG. 17A and FIG. 17B are side views showing a light convergence with (A) a small coefficient k and a light convergence with (B) a large coefficient k.
Figure 17B:
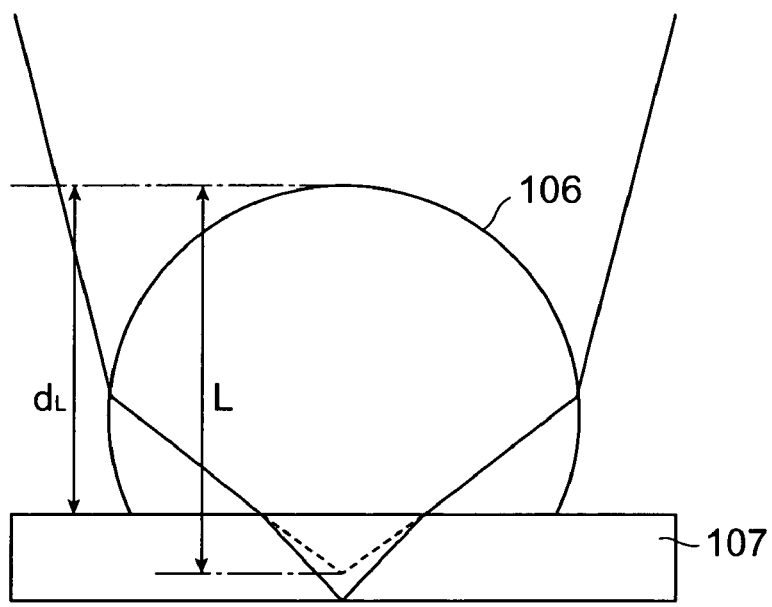

Herein, FIG. 17A and FIG. 17B are side views showing a light convergence with (A) a small coefficient k and a light convergence with (B) a large coefficient k. As shown in FIG. 17A and FIG. 17B, in a case where the coefficient k is set small, for example, in a case where the k is set within the above-described range of 0<k≦0.5, a light path of light viewed from the SIL is widened compared to a case with a large coefficient k. In such a case, it is preferable to select a lens with a great numerical aperture NA as an objective lens to be combined with the SIL.

Figure 18:
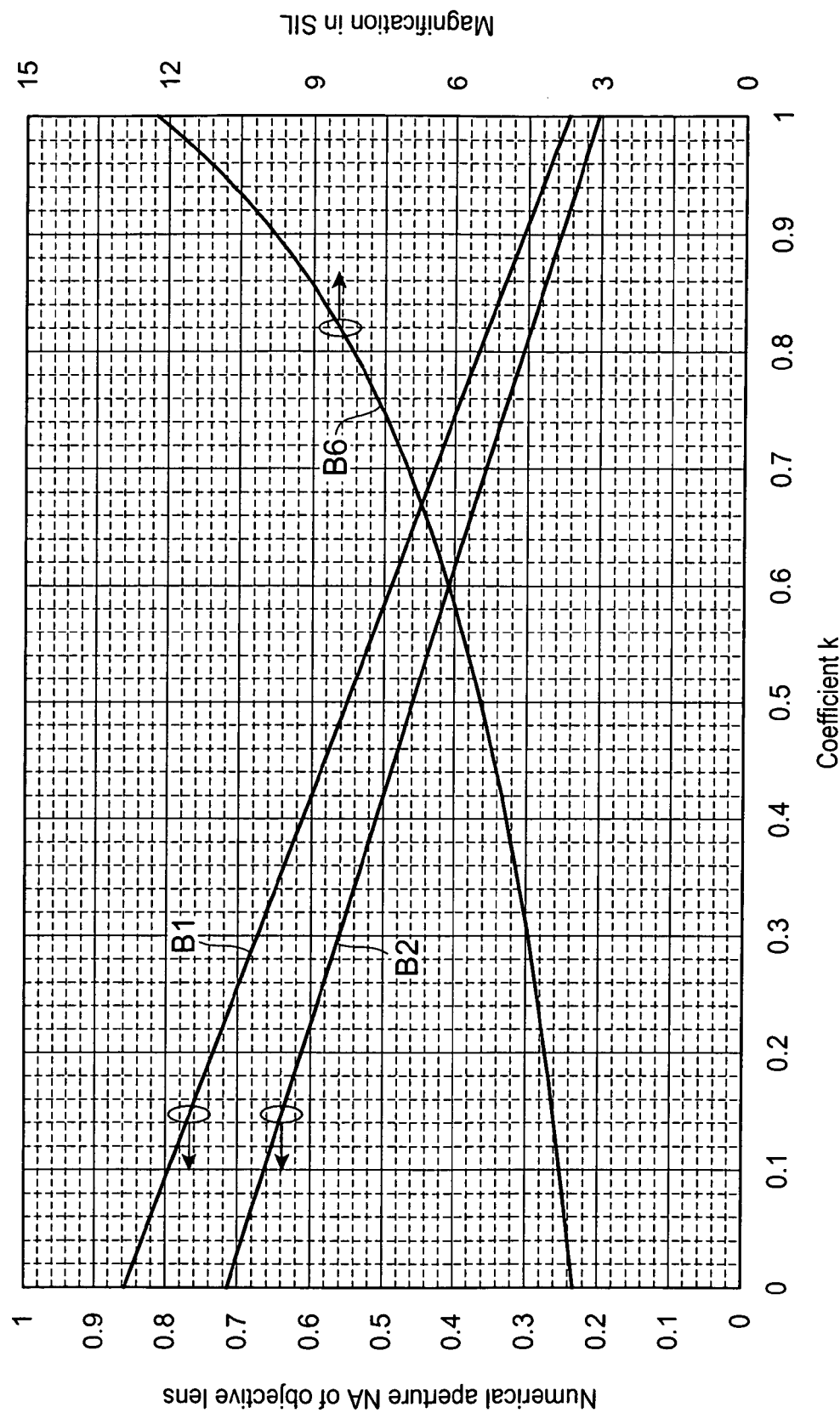
FIG. 18 is a graph showing an example of correlation between the coefficient k value of an SIL and numerical aperture NA required in an objective lens.

FIG. 18 is a graph showing an example of correlation between the coefficient k value of an SIL and numerical aperture NA required in an objective lens. In this graph, the horizontal axis shows a coefficient k set in the SIL and the vertical axis shows a numerical aperture NA of the objective lens. In this graph, a refractive index of the SIL is provided as $n_L = 3.5$ (material Si). Moreover, the plotted graph B1 shows a required NA of the objective lens when an NA attained on the optical axis in an SIL is provided as 3.0, and the plotted graph B2 shows a required NA for the objective lens when an NA attained on the optical axis in an SIL is provided as 2.5. In addition, in this graph, magnification in an SIL corresponding to the coefficient k value is collectively shown by the plotted graph B6.

As shown in these plotted graphs B1 and B2, when the attained NA in the SIL is increased, a required NA of the objective lens also increases accordingly. In addition, when the attained NA in the SIL is fixed, as mentioned above with regard to FIG. 17A and FIG. 17B, when the coefficient k value decreases, NA required in the objective lens increases. Accordingly, when setting a coefficient k value in the SIL, it is also necessary to consider a combination with the objective lens, as well.

Figure 19:
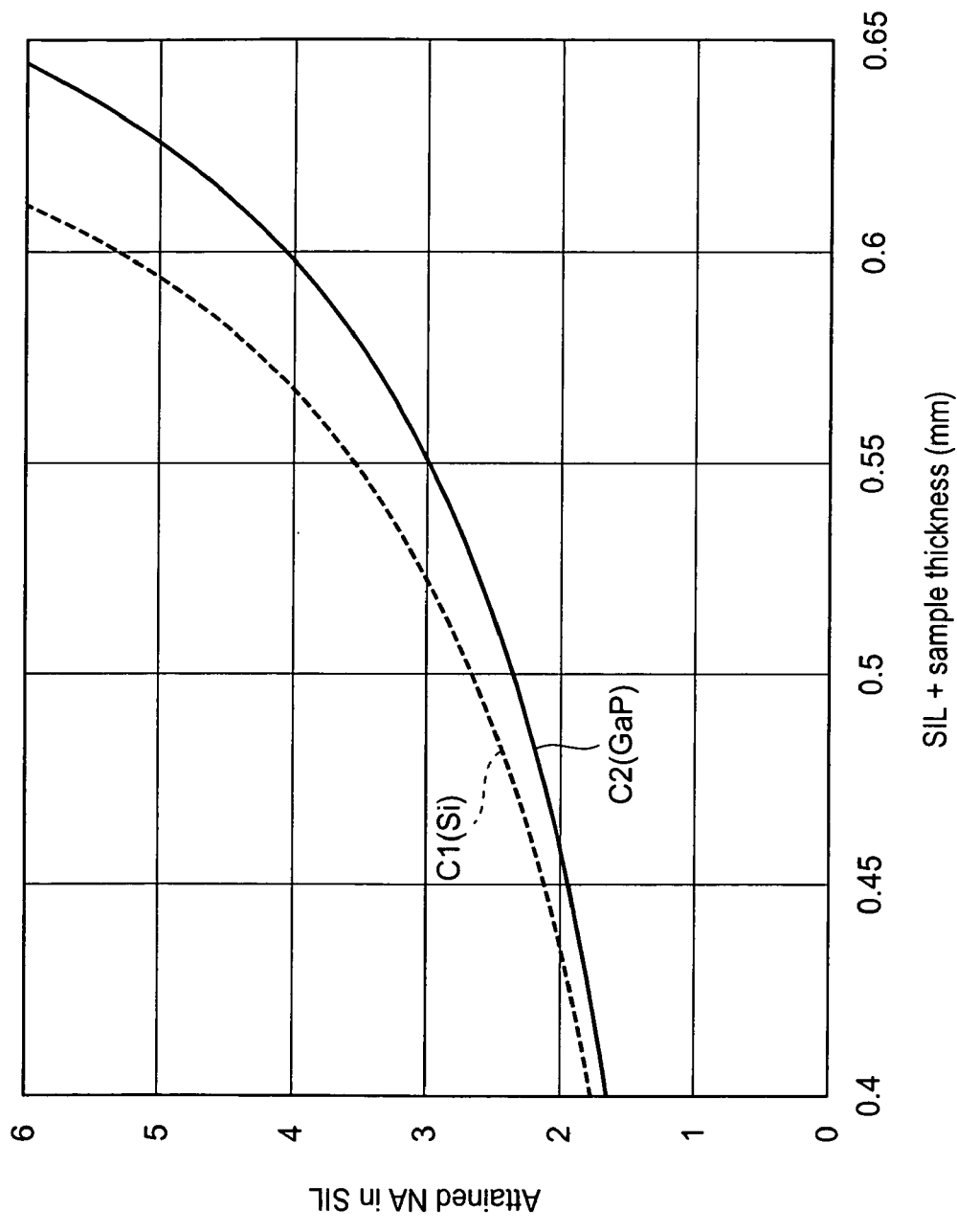
FIG. 19 is a graph showing an example of correlation between the SIL+sample thickness and attained NA in an SIL on the optical axis.

In addition, FIG. 19 is a graph showing an example of correlation between the SIL+sample thickness and attained NA on the optical axis in an SIL. In this graph, the horizontal axis shows a thickness (mm) of the SIL+sample (Si substrate)

from the SIL vertex, and the vertical axis shows an attained NA on the optical axis in the SIL. In this graph, the radius of curvature of the SIL is provided as $R_L=0.5$ mm, and the NA of the objective lens is provided as 0.76. In addition, the plotted graph C1 shows an attained NA when the material of the SIL is Si, and C2 shows an attained NA when the material of the SIL is GaP. As such, in a case where the NA of the objective lens is fixed, as the SIL+sample thickness increases, the attained NA increases.

In actuality, the NAs of the SIL and objective lens can be appropriately selected according to the detailed constructions, and for example, an attained NA of the SIL is on the order of 2.5-3.0, and an NA of the objective lens is on the order of 0.76. In addition, as the objective lens, a normal objective lens can be employed, and magnification thereof is on the order of 50 times, for example.

Figure 20:
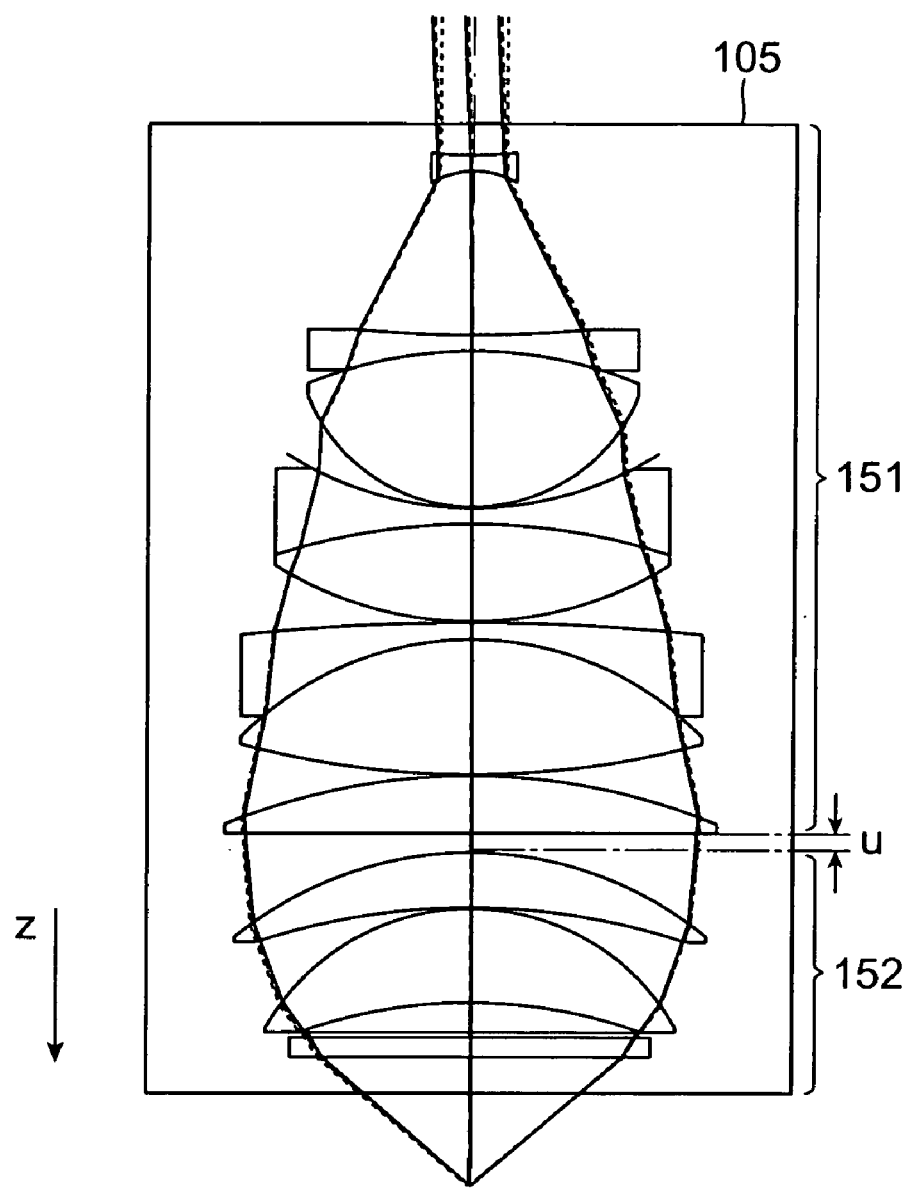
FIG. 20 is a side sectional view showing an objective lens construction.

In addition, in order to reduce chromatic aberration, in a case where the k is set within the above-described range of $0<k\leq0.5$, it is preferable that geometrical aberration characteristics thereof can be corrected by the objective lens-side. As such an objective lens, an objective lens having a construction shown in a side sectional view of FIG. 20 exists. This objective lens 105 is composed of, as lens groups thereof, two lens groups of a first lens group 151 and second lens group 152 disposed along the optical axis. In addition, a lens interval u of these lens groups 151 and 152 is changeable by rotating a correction ring (unillustrated) provided on the outer circumferential portion of the objective lens 105. By employing an objective lens 105 having such a construction, geometrical aberration characteristics (for example, spherical aberration) can be corrected by the objective lens 105 side.

Here, in a case where an objective lens with a correction ring is used in combination with an SIL as such, it is preferable to set a coefficient k within a range where spherical aberration through the SIL can be corrected by the correction ring of the objective lens. For example, in the objective lens having a construction of FIG. 20, where a refractive index of the SIL is $n_L=3.1$, radius of curvature is $R_L=0.5$ mm, and a refractive index of the sample is $n_s=3.5$, if the sample thickness is on the order of $t_s=0.03$ mm, a spherical aberration correction is possible by the correction ring with a condition on the order of $0<k<0.4$, and if on the order of $t_s=0.15$ mm, with a condition on the order of $0<k<0.2$.

In addition, the coefficient k may be set in a range of $0.7\leq k<1$. In this case, the SIL can be combined with a low-NA objective lens. However, since a great chromatic aberration occurs with a normal objective lens, it is necessary to use a specially designed objective lens for application other than monochromatic laser light.

The solid immersion lens and a microscope according to the present invention can be used as a solid immersion lens whose positional control is easy, which can allow a light flux with a high numerical aperture to pass, and furthermore where there is no danger of damaging an observed object or itself, and a microscope using the same.

In addition, in a case where geometrical aberration characteristics through a solid immersion lens are evaluated to set a coefficient k ($0<k<1$) so as to satisfy predetermined conditions, and a solid immersion lens and an observing method using, as a sample observing surface, a surface which includes a point positioned on the downstream side by $k\times(R_L/n_L)$ along the optical axis from the sphere center of a spherical optical surface of a solid immersion lens and is approximately orthogonal to the optical axis are provided, it becomes possible to, while widening a field of view available for an observation, satisfactorily observe a sample image. In addition, in a case where a lens shape is set while taking the reflective index $n_s$ and thickness $t_s$ of a sample into consideration, it becomes possible to satisfactorily observe a desirable observing position of the sample.

What is claimed is:

1. A solid immersion lens to be positioned on an optical axis from an observed object to an optical system for leading an image of the observed object, including an objective lens into which light from the observed object is made incident, and to be used for an observation of the observed object, comprising:
    a spherical surface; and
    a bottom surface including an attaching surface to be attached to the observed object,
    wherein
    the attaching surface of the solid immersion lens to the observed object is formed in a toroidal shape.

2. The solid immersion lens as set forth in claim 1, wherein when a to-be-attached surface of the observed object is set to an X-Y plane, a ratio of a radius of curvature in the X-direction of the toroidal shape to a radius of curvature in the Y-direction greater than the radius of curvature in the X-direction is provided as $1:3\sim1:\infty$.

3. The solid immersion lens as set forth in claim 1, wherein an attaching surface to the observed object is formed in a cylindrical shape.

4. The solid immersion lens as set forth in claim 1, wherein an attaching surface to the observed object receives a hydrophilic treatment.

5. The solid immersion lens as set forth in claim 1, wherein the solid immersion lens is formed of a material with a refractive index $n_L$ while having a spherical optical surface with a radius of curvature $R_L$, a distance along an optical axis from the vertex to a virtual observing surface when a refractive index of the observed object is equalized to the refractive index $n_L$ is provided, by a coefficient k ($0<k<1$) set so that geometrical aberration characteristics satisfy predetermined conditions, as $L=R_L+k\times(R_L n_L)$, and
    when the refractive index of the observed object is provided as $n_s$ and a thickness of the observed object to an actual observing surface is provided as $t_s$, a thickness along the optical axis satisfies $d_L=L-t_s\times(n_L/n_s)$.

6. The solid immersion lens as set forth in claim 5, wherein the thickness of the observed object to the actual observing surface is $t_s=0$, and the thickness along the optical axis is $d_L=L=R_L+k\times(R_L/n_L)$.

7. The solid immersion lens as set forth in claim 5, wherein the coefficient k is a value within a range of $0.5<k<0.7$.

8. The solid immersion lens as set forth in claim 5, wherein the coefficient k is a value within a range of $0<k\leq0.5$.

9. A microscope for observing an observed object, comprising:
    an optical system for leading an image of the observed object, including an objective lens into which light from the observed object is made incident; and
    the solid immersion lens as set forth in claim 1, and positioned on the optical axis from the observed object to the optical system.

10. A microscope as set forth in claim 9, further comprising:
    an optical coupling material dripping unit for dripping an optical coupling material on an observation point of the observed object.

* * * * *